US008870846B2

(12) United States Patent
Davis et al.

(10) Patent No.: US 8,870,846 B2
(45) Date of Patent: Oct. 28, 2014

(54) SYSTEMS AND METHODS FOR PROVIDING A CLOSED VENTING HAZARDOUS DRUG IV SET

(71) Applicant: Becton, Dickinson and Company, Franklin Lakes, NJ (US)

(72) Inventors: Bryan G. Davis, Sandy, UT (US); Minh Quang Hoang, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/738,889

(22) Filed: Jan. 10, 2013

(65) Prior Publication Data
US 2013/0102974 A1 Apr. 25, 2013

Related U.S. Application Data

(62) Division of application No. 12/775,128, filed on May 6, 2010, now Pat. No. 8,366,658.

(51) Int. Cl.
A61M 31/00 (2006.01)
A61M 5/165 (2006.01)
A61M 39/20 (2006.01)
A61M 5/38 (2006.01)
A61M 5/162 (2006.01)
A61M 5/14 (2006.01)

(52) U.S. Cl.
CPC .............. A61M 5/162 (2013.01); A61M 5/165 (2013.01); A61M 39/20 (2013.01); A61M 2005/1402 (2013.01); A61M 5/38 (2013.01); A61M 2202/049 (2013.01); A61M 5/1411 (2013.01)

USPC ............ 604/506; 604/82; 604/126; 604/246; 604/257

(58) Field of Classification Search
CPC ... A61M 5/1411; A61M 5/162; A61M 5/165; A61M 5/38; A61M 39/20; A61M 2005/1402
USPC ..................... 604/80–87, 122, 126, 247, 251, 604/288.01–288.04, 246, 257, 506
See application file for complete search history.

(56) References Cited

U.S. PATENT DOCUMENTS 4,013,072 A 3/1977 Jess
4,685,912 A * 8/1987 Jones ............................ 604/247

(Continued)

FOREIGN PATENT DOCUMENTS

EP 0 102 748 A2 3/1984
EP 1 535 641 A1 6/2005
GB 1 182 016 2/1970

OTHER PUBLICATIONS

"Closed Male Connector, Safe Preparation and Delivery of Hazardous Drugs," Spiros, pp. 1-2.

(Continued)

Primary Examiner — Theodore Stigell
(74) Attorney, Agent, or Firm — Jeanne Lukasavage; Craig Metcalf; Kirton McConkie

(57) ABSTRACT

A device for priming and venting a hazardous drug within an intravenous administration set. The device includes various access ports and fluid channels to permit direct injection of a hazardous drug into the fluid reservoir, while eliminating the possibility of undesirable exposure to the hazardous drug. The device further includes priming and flushing ports to enable flushing of a hazardous drug from the system following an infusion procedure.

18 Claims, 17 Drawing Sheets

(56) References Cited

U.S. PATENT DOCUMENTS

| | | | |
|---|---|---|---|
| 4,734,091 | A | 3/1988 | Boyle et al. |
| 4,795,429 | A | 1/1989 | Feldstein |
| 4,998,926 | A | 3/1991 | Alchas |
| 5,423,346 | A | 6/1995 | Daoud |
| 5,489,385 | A | 2/1996 | Raabe et al. |
| 5,779,674 | A | 7/1998 | Ford |
| 6,261,267 | B1 | 7/2001 | Chen |
| 6,409,708 | B1 * | 6/2002 | Wessman .................. 604/284 |
| 7,722,577 | B2 | 5/2010 | Miner |
| 8,366,658 | B2 | 2/2013 | Davis et al. |
| 2005/0171491 | A1 | 8/2005 | Minh Miner et al. |
| 2006/0189937 | A1 | 8/2006 | Miner |
| 2008/0097315 | A1 * | 4/2008 | Miner et al. .................. 604/122 |
| 2008/0319422 | A1 * | 12/2008 | Cardenas ...................... 604/537 |
| 2010/0063445 | A1 * | 3/2010 | Sternberg et al. ............. 604/122 |

OTHER PUBLICATIONS

"Performance of the OnGuard CMS with Tevadaptor Components," Braun, p. 1, 2007.

"Texium Closed Maile Luer User Guide," Cardinal Health, p. 1, 2006-2007.

* cited by examiner

SYSTEMS AND METHODS FOR PROVIDING A CLOSED VENTING HAZARDOUS DRUG IV SET

RELATED APPLICATIONS

This application is a divisional application of U.S. application Ser. No. 12/775,128, filed on May 6, 2010 and issued as U.S. Pat. No. 8,366,658 on Feb. 5, 2013, entitled SYSTEMS AND METHODS FOR PROVIDING A CLOSED VENTING HAZARDOUS DRUG IV SET, and is incorporated herein.

BACKGROUND OF THE INVENTION

The present invention relates to systems and methods for priming an intravenous (IV) administration set with a hazardous drug or chemical, as commonly used in the medical and infusion therapy fields.

An IV administration set is typically used to deliver to or retrieve from a patient a fluid, such as blood, a medicament, a nutritional supplement, or a solution. In some areas of medicine, treatment of disease and illness requires infusion of hazardous chemicals, such as toxic chemotherapeutic agents. The hazardous drugs are typically added to a fluid reservoir, such as an IV bag, and then administered to the patient via a patient conduit and an intravenous needle. Prior to administering the hazardous solution to the patient, air within the patient conduit must be purged to prevent infusion of the air into the patient.

Standard priming procedures entail squeezing a drip chamber portion of the IV administration set to initiate flow of the hazardous drug from the fluid reservoir. Once flow is initiated, the hazardous drug continues through patient conduit thereby displacing air within the conduit. However, in addition to displacing air from the conduit, the flow of the hazardous drug also displaces hazardous vapors produced from the hazardous drug. Exposure to the displaced hazardous vapors may result in illness, dizziness, nausea, vomiting, seizures, unconsciousness, and even death. Additionally, the clinician must carefully monitor the priming process to ensure that the hazardous drug does not exit the patient conduit. Direct exposure to the hazardous drug may also result in the abovementioned side effects.

Thus, while techniques currently exist that are used for priming an IV administration set for use with a hazardous drug, challenges still exist. Accordingly, it would be an improvement in the art to augment or even replace current techniques with other techniques.

BRIEF SUMMARY OF THE INVENTION

The present invention relates to systems and methods for providing a closed venting system for use in priming an intravenous (IV) administration set with a hazardous drug or chemical. Specifically, the present invention relates to an IV delivery system incorporating various ports and fluid channels designed to minimize exposure to a hazardous drug or vapor within the IV delivery system.

The IV delivery system generally includes a coupling assembly for attaching a drip chamber to a fluid reservoir, such as an IV bag. In some embodiments the coupling assembly includes a first fluid channel providing fluid communication between the fluid reservoir and the drip chamber of the delivery system. In other embodiments, the coupling assembly further includes a second fluid channel providing fluid communication between the fluid reservoir and an external access port. The external access port is coupled to an outer surface of the coupling assembly or drip chamber and provides direct access to the fluid reservoir. In some embodiments, the access port is accessed by a syringe to deliver a hazardous drug to the fluid reservoir via the second fluid channel. In other embodiments, the access port further includes a valve or septum to seal the second fluid channel.

The IV set further includes a drip chamber fixedly attached to an output of the first fluid channel. The drip chamber generally includes a closed container configured to receive fluid from the fluid reservoir. In some embodiments of the present invention, the drip chamber further includes an external priming port. The priming port is coupled to an outer surface of the drip chamber, and is in fluid communication therewith. In some embodiments, a priming solution is injected into the drip chamber via the priming port. The injected priming solution may be useful in priming a patient conduit prior to infusion, or may be useful in flushing the patient conduit to remove residual hazardous drug following the infusion procedure.

In other implementations of the present invention, the drip chamber and patient conduit of the IV administration set are primed with the hazardous drug contained within the fluid reservoir. In some embodiments, undesirable exposure to the hazardous drug during the priming process is prevented by inserting a terminal end of the patient conduit into the access port of the coupling assembly. Thus, as the patient conduit is primed, hazardous fumes are vented into the fluid reservoir via the access port. In this manner, exposure to the hazardous molecules is avoided.

In some embodiments of the present invention, residual hazardous drug within the IV delivery system is flushed from the system via a flush port. The flush port is generally positioned on an external surface of the IV delivery system upstream from the infusion site of the patient. In some embodiments, a syringe or other delivery device is coupled to the flush port to deliver a priming or flushing fluid into the IV delivery system. As such, the priming fluid flushes residual hazardous drug from the delivery system and into the patient. Further, in some embodiments, undesirable exposure to the hazardous drug is prevented by inserting the terminal end of the patient conduit into a container, or a filtration system during the priming process.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 3:
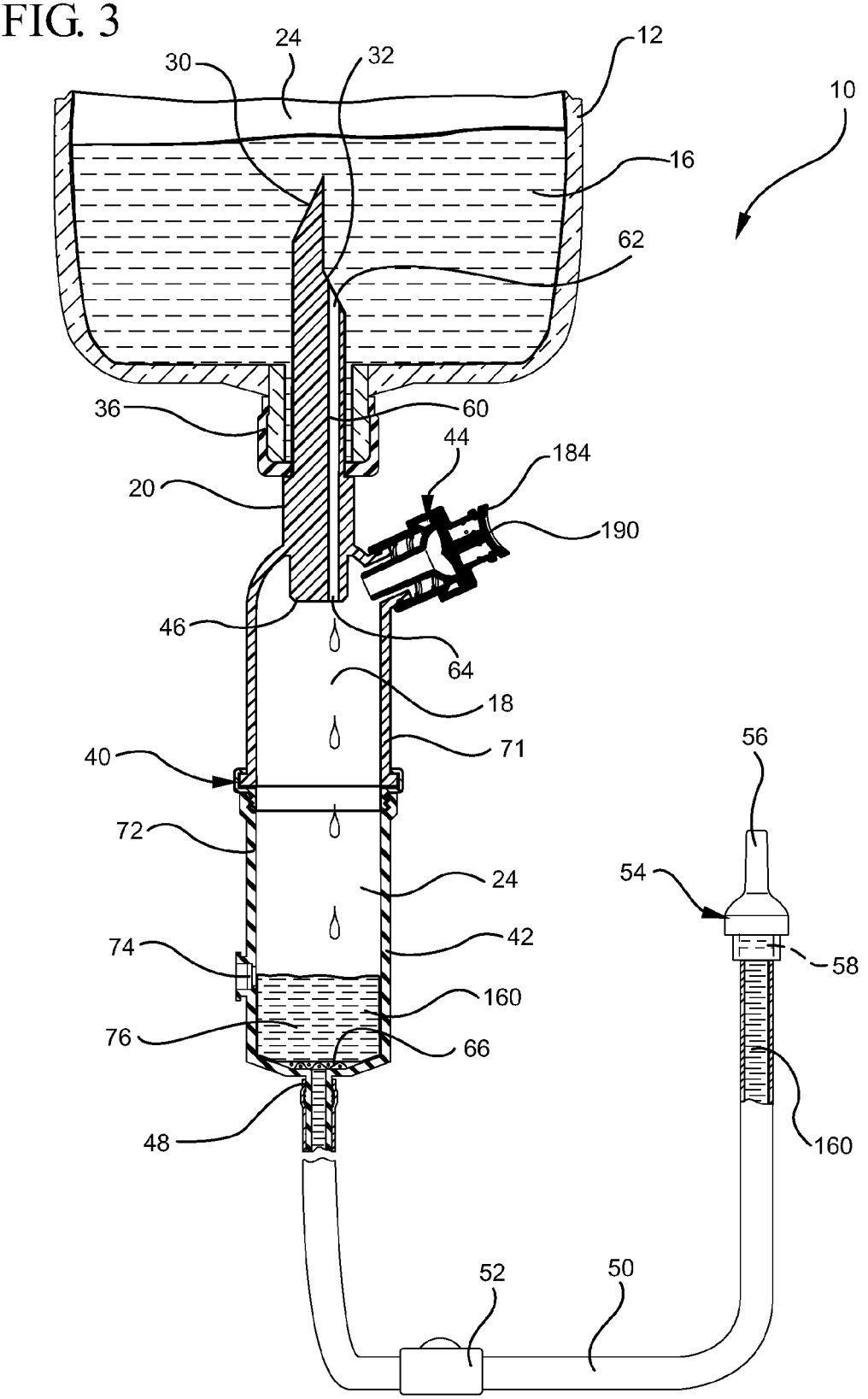
FIG. 3 is a cross-section view of an implementation of an IV set of the present invention coupled to an IV bag.

Referring now to FIG. 1, an implementation of an intravenous (IV) delivery system 10 is shown. Some embodiments of the IV delivery system 10 include a coupling assembly 20 having a spike 30 configured for insertion into a fluid reservoir 12, as shown in FIG. 3. Some implementations of the coupling assembly 20 comprise a rigid, polymer material such as polystyrene, polyester, or polypropylene. Some embodiments of the spike 30 member further include a chamfered end surface 32 to aid insertion of the coupling assembly 20 into a fluid reservoir 12.

In some embodiments, the coupling assembly 20 further includes a first fluid channel 60. The first fluid channel 60 provides a fluid pathway between a coupled fluid reservoir 12 and the drip chamber 40 of the IV delivery system 10. The first fluid channel 60 includes an input 62 and an output 64. With reference to FIG. 3, the input 62 is positioned within the fluid reservoir 12, and the output 64 is coupled to an input 46 of the drip chamber 40. The output 64 of the first fluid channel 60 is positioned adjacent to the drip chamber 40 such that the fluid 16 from the fluid reservoir 12 is collected in the drip chamber 40 via the output 64. In some embodiments, the output 64 further includes a tapered opening which enables the fluid 16 to form into drops 18 prior to being collected in the drip chamber 40.

The drip chamber 40 is generally configured to receive fluid 16 dispensed from the output 64 of the first fluid channel 60. As previously discussed, the output 64 is configured to permit the fluid 16 to form into drops 18 as the fluid 16 leaves the output 64. In some embodiments, the drip chamber 40 is generally cylindrical having an upper, rigid portion 71 sealedly coupled to a lower, flexible portion 72. In some embodiments, manipulation of the flexible portion 72 of the drip chamber 40 initiates flow of a fluid or hazardous drug 16 from the fluid reservoir 12 into the drip chamber 40. This process requires that the system 10 first be sealed by inserting the spike 30 into a sealed fluid reservoir 12, and occluding a patient conduit 50 via a roller clamp 52, or similar clamping device. A vacuum is created in the drip chamber 40 by compressing and releasing the flexible portion 72 of the drip chamber 40. This compression displaces air within the drip chamber 40 into the fluid reservoir 12, thus creating a negative pressure, or vacuum within the drip chamber 40. The negative pressure in the drip chamber draws hazardous drug 16 from the fluid reservoir 12 into the fluid reservoir 40 to form a second fluid reservoir 42 within the drip chamber 40, as is conventional. Once the roller clamp 52 is released, hazardous fluid 16 continues to flow from the fluid reservoir 12 due to gravity. One of skill in the art will appreciate that other methods may be used to initiate flow of the hazardous fluid 16 through the system, including gravity-feed methods, or methods utilizing a peristaltic pump.

Referring again to FIG. 1, some embodiments of the present invention further include a self-sealing priming/flushing port 44. The priming/flushing port 44 is coupled to an outer surface of the drip chamber 40. In some embodiments, the priming/flushing port 44 is positioned above the second fluid reservoir 42. In other embodiments, the priming/flushing port 44 is positioned adjacent to, or within the second fluid reservoir 42 portion of the drip chamber 40. The flushing/priming port 44 is in fluid communication with the interior of the drip chamber 40 and is designed to compatibly receive a syringe 180 or other device configured to deliver a priming/flushing solution 160 directly to the drip chamber 40. In some embodiments, the priming/flushing port 44 includes an opening 190 for receiving a tip portion 182 of a syringe 180. The priming/flushing port 44 further includes a valve or split septum 184 which is biased to an opened position by inserting the tip 182 into the opening 190. Prior to insertion of the tip portion 182, the valve or septum 184 forms an airtight seal, thereby maintaining pressure within the drip chamber 40 and the remainder of the IV delivery system 10.

Figure 2:
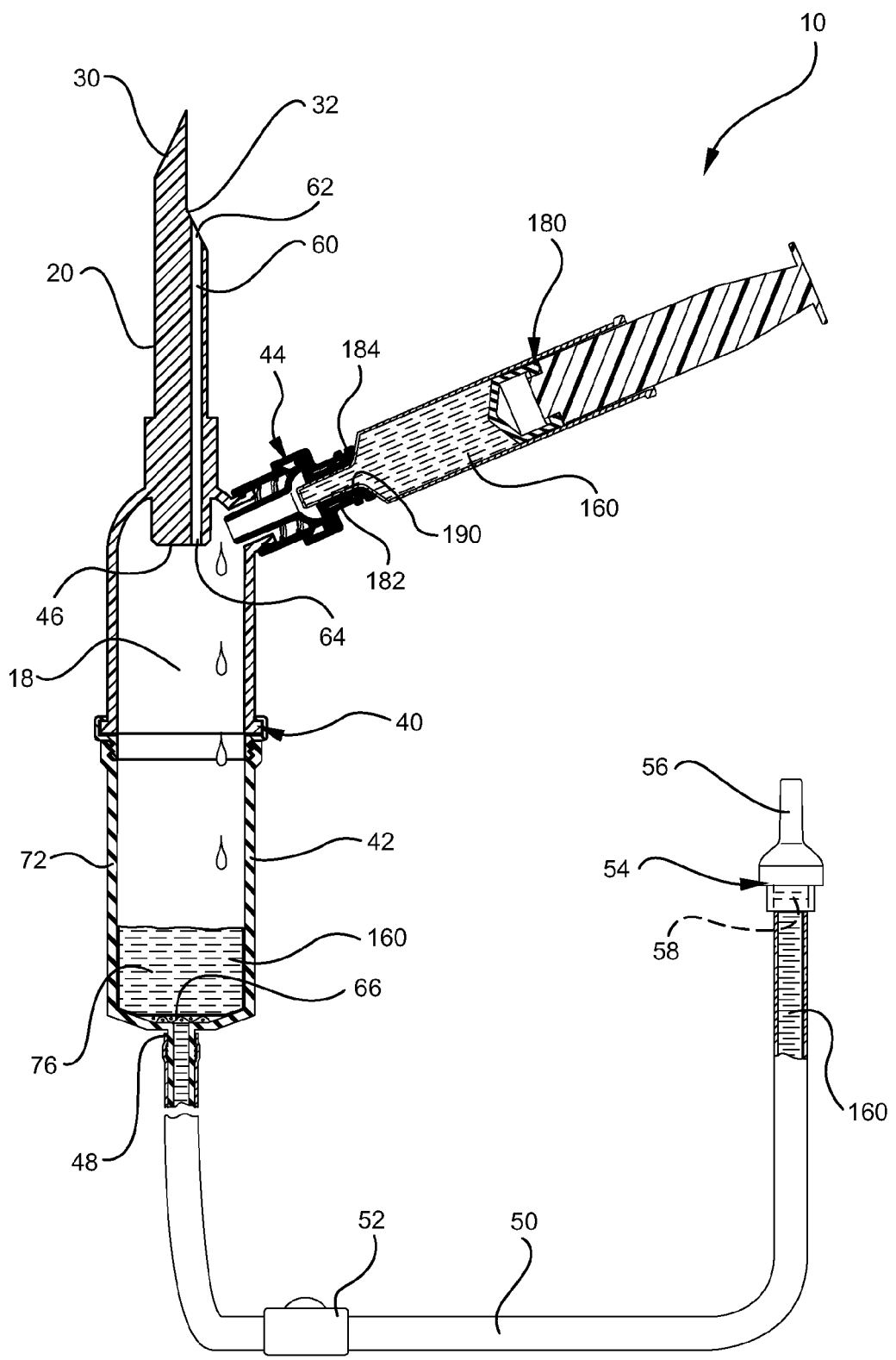
FIG. 2 is a cross-section view of an implementation of an IV set of the present invention being primed with a priming solution via the priming port.

In some embodiments, the drip chamber 40 and patient conduit 50 are pre-primed with a priming solution 160 via the priming/flushing port 44. Referring now to FIG. 2, the drip chamber 40 is accessed via the priming/flushing port 44 with a syringe 180 containing a priming fluid 160. In some embodiments, the priming fluid 160 is a sterile solution of water containing a non-hazardous additive, such as sodium chloride or dextrose. The process of priming the drip chamber 40 and the patient conduit 50 purges air from these components thereby preventing the possibility of air being infused into a patient during the infusion process.

In some embodiments, the IV delivery system 10 further includes a membrane 66 disposed in the drip chamber 40. The membrane 66 is configured such that air is prevented from leaving the drip chamber 40 into the patient conduit 50. Thus, the membrane 66 acts as a bubble trap to trap any air bubbles that may otherwise flow out of the drip chamber 40 and into the patient conduit 50. As illustrated in FIGS. 1-3, the drip chamber 40 is connected to a patient conduit 50. Conduit 50 comprises a tube used to convey fluid 160 from the drip chamber 40 and the first fluid reservoir 12 to the patient 100.

The membrane 66 is positioned in the bottom portion of the drip chamber 40 so as to completely cover the drip chamber output 48. By positioning the membrane 66 to completely cover the chamber output 48, air is prevented from being trapped between the membrane 66 and the output 48 as the priming fluid 160 moves through the membrane 66. Additionally, in some embodiments the membrane 66 comprises a hydrophilic material that is configured to strongly interact with the fluid 16 thereby trapping the fluid 160 within the membrane 66. In some embodiments, membrane 66 comprises at least one of polytetrafluoroethylene, hydrophilic nylon, hydrophilic polypropylene, hydrophilic polyethersulfone or a nonwoven material coated with the above materials. As fluid 160 flows from the drip chamber 40 through the membrane 66, fluid 160 trapped within the membrane 66 is displaced by incoming fluid 160, and the displaced fluid 160 is forced into the patient conduit 50. However, when the drip chamber 40 runs dry, or when the supply of fluid 160 from the drip chamber 40 is exhausted, the fluid 160 within the membrane 66 is retained and flow through the patient conduit 50 ceases. Thus, air within the drip chamber 40 is prevented from passing through the membrane 66 and into the patient conduit 50.

In some embodiments, a roller clamp 52, or other clamping device, as well as a flow control plug or vent membrane 58 may also be attached to the patient conduit 50. For example, in some embodiments membrane 58 is coupled to the patient conduit 50 via a coupling means, such as a luer connector or a friction interface. Clamp 52 permits the flow of fluid 160 exiting the drip chamber 40 to be controlled and stopped. In some embodiments, the clamp is preprogrammed to allow fluid 160 to flow at a specific rate. In other embodiments, clamp 52 is used in combination with a pump or other device (not shown) configured to limit the flow rate of fluid 160.

Figure 1A:
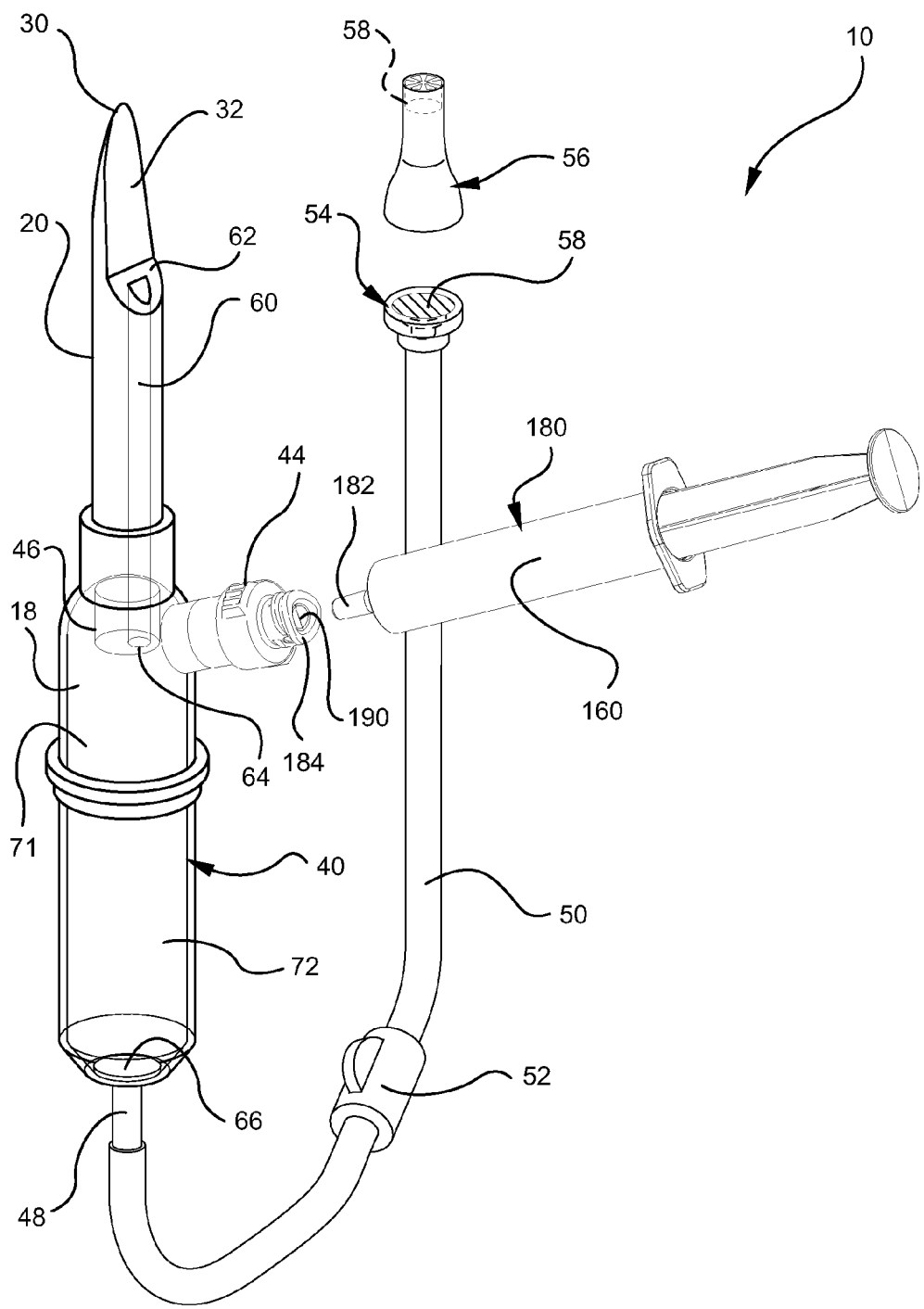
FIG. 1A is a perspective view of an implementation of an IV set having a priming port.
Figure 1B:
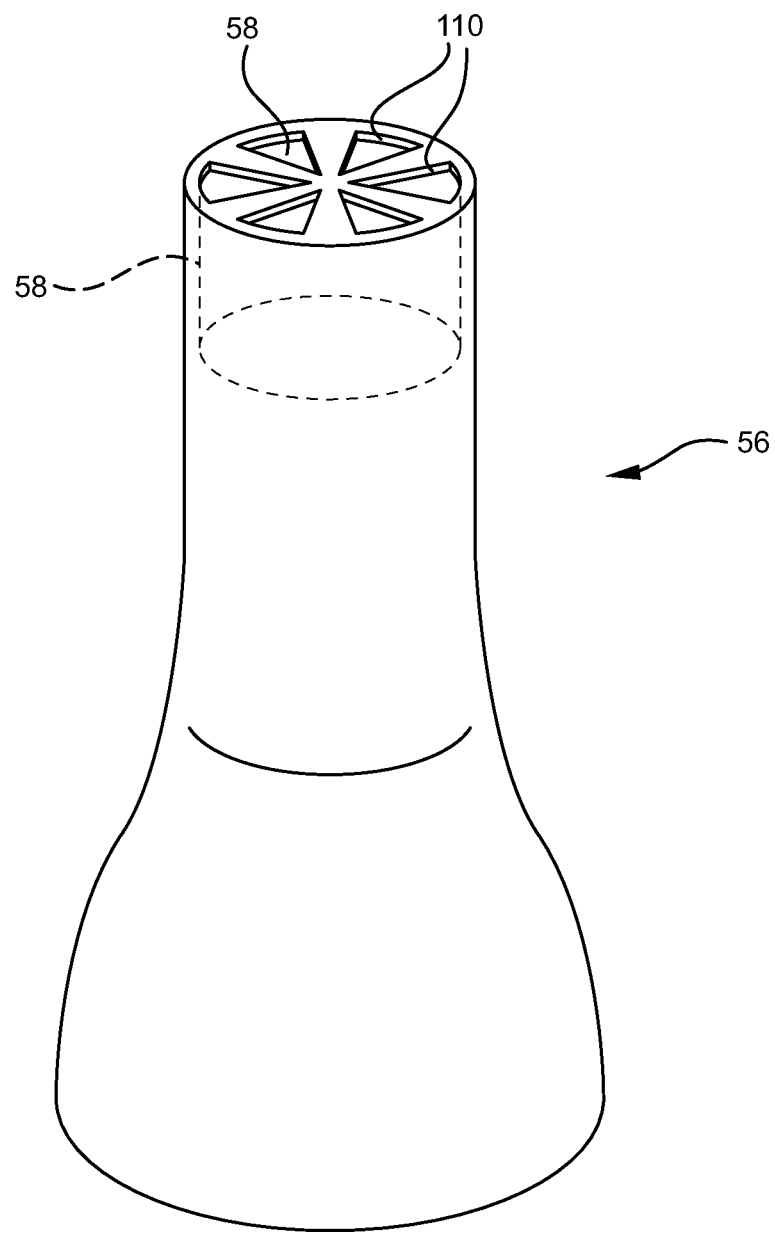
FIG. 1B is a perspective view of an implementation of a vented cap in accordance with a representative embodiment of the present invention.

Vent membrane 58 generally comprises a material or combination of materials necessary to provide various functions. In some embodiments, vent membrane 58 is coupled directly to terminal end 54 of the intravenous tubing 50. In other embodiments, end 54 is configured to include a recess or other feature to receive vent membrane 58, such as a casing. In other embodiments, a dust cap 56 is modified to include a vent membrane 58, as shown in FIG. 1B. Dust cap 56 may also include a plurality of vents 110 configured to retain membrane 58, yet permit passage of air through membrane 58.

Vent membrane 58 may be configured to provide various functions as required by IV delivery system 10. For example, in some embodiments vent membrane 58 is provided as a contaminant filter to protect end 54 from external contaminants. In other embodiments, vent membrane 58 is provided as a hydrophobic air filter configured to permit venting of air within the delivery system, yet prevent passage of fluids 160.

In some embodiments, vent membrane 58 comprises a porous material, such as polytetrafluoroethylene, having a plurality of pores sized and configured to permit the passage of air, yet prevent the passage of larger molecules, such as a fluid, a hazardous solution, or a hazardous solute. In other embodiment, vent membrane 58 comprises a plurality of pores sized approximately 0.1 to 0.5 microns thereby allowing air to pass through the pores, yet preventing the passage of fluids and larger aerosolized particles or hazardous drug molecules within the system 10. Thus, during the priming process of the system 10, air within the patient conduit 50 is permitted to exit the conduit 50 through vent membrane 58 while the fluid 160 and hazardous gasses 24 are retained in the conduit 50. Following the priming process, clamp 52 is engaged to occlude conduit 50. Once occluded, terminal end 54 of the conduit 50 is coupled to the patient via a catheter 102, or a secondary IV line (not shown).

In some embodiments, vent membrane 58 comprises a 360° membrane that is designed to minimize potential for passing of aerosolized or gas form of hazardous drugs that come in contact with the plug 58 during the priming process. Vent membrane 58 is thus configured to permit passage of non-toxic air within the patient conduit 50, yet includes structural or chemical features to restrict passage of larger, toxic molecules. These features may include any technology or device capable of providing such restrictions.

For example, in some embodiments the material of the vent membrane 58 comprises at least one of polytetrafluoroethylene, hydrophilic nylon, hydrophilic polypropylene, hydrophilic polyethersulfone or a nonwoven material coated with the above materials. The vent membrane 58 further includes restricted porosity, as discussed above, thereby limiting the passage of larger molecules. In other embodiments, the vent membrane 58 comprises a catalyst, such as activated charcoal, which bonds to the hazardous drug molecules thereby sequestering the hazardous molecules within the plug 58. In other embodiments, the vent membrane 58 comprises a composite of alternating layers of PTFE and activated carbon or charcoal.

The flow rate of a fluid 160 through the conduit 50 is determined by the rate at which air within the conduit is permitted to flow through the vent membrane 58. Thus, the flow of the fluid 160 through the conduit 50 may be adjusted by increasing or decreasing the number and size of the pores of the plug 58. For example, in some embodiments the flow rate of the vent membrane 58 is increased by either increasing the diameter of the pores, or by increasing the number of pores. In another embodiment the flow rate of the vent membrane 58 is decreased by either decreasing the diameter of the pores, or by decreasing the number of pores.

Figure 4:
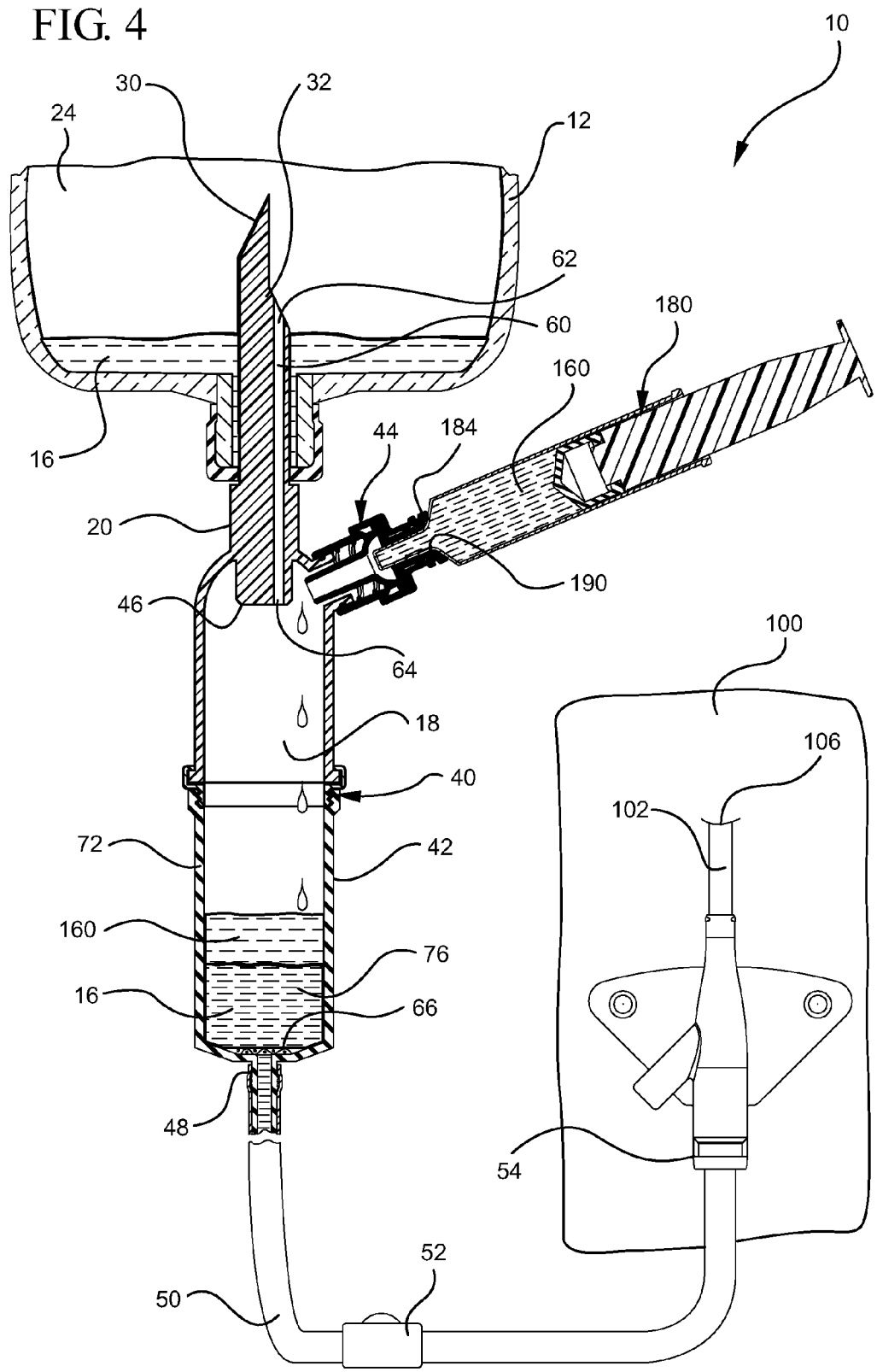
FIG. 4 is a cross-section view of an implementation of an IV set of the present invention being flushed with a priming solution via the priming port, following infusion of a hazardous drug.

In some embodiments, the flow rate of air through the vent membrane 58 is configured to be equal to or less than the flow rate of the fluid 160 through the membrane 66. Thus, in some embodiments, the flow rate of the membrane 66 and the flow rate of the vent membrane 58 are matched to ensure proper, air-bubble-free flow of the fluid 160 through the system 10. In some embodiments, the flow rates of the membrane 66 and the vent membrane 58 are matched to ensure that fluid 160 flow through the membrane 66 at a rate that is slightly slower than the rate at which the air vents through the vent membrane 58. As such, the fluid 160 forms a pool 76 in the second fluid reservoir 42, as shown in FIGS. 2-4.

Pool 76 of fluid 160 provides a continuous, bubble-free fluid source that flows from the drip chamber 40 and through the conduit 50 displacing air entrapped therein. In other embodiments, the flow rate of the vent membrane 58 is configured to be slower than the flow rate of the membrane 66 such that the flow velocity of the fluid 160 through the conduit 50 is slowed to an optimum flow rate. In some embodiments, an optimum flow rate is the rate at which fluid 160 will efficiently and thoroughly displace air within the conduit 50 during the priming process.

In those embodiments that are configured to incorporate a membrane 66 and a vent membrane 58, the process of priming the system 10 does not require use of the roller clamp 52, or any similar clamping device as is conventional. Rather, the combination of the membrane 66 and the vent membrane 58 enable automatic priming of the system 10. Specifically, once the priming fluid 160 is introduced to the drip chamber 40, the fluid 160 automatically flows through the membrane 66 and the conduit 50 until it reaches the vent membrane 58. In some embodiments, the drip chamber 40 further includes a vent 74 whereby a negative pressure within the drip chamber 40 is equalized to permit automatic flow of the fluid 160 through the membrane 66.

The position of the vent 72 on the drip chamber 40 is selected so as to determine the height of the second fluid reservoir 42. Thus, as the fluid 16 flows into the drip chamber 40, the height of the fluid 16 is prevented from exceeding the positioned height of the vent 74. When the height of the second fluid reservoir 42 exceeds the positioned height of the vent 74, the vent 74 is blocked by the fluid 16 and is thereby prevented from venting and/or equalizing pressure within the drip chamber 40. As such, positive pressure builds within the drip chamber 40 preventing fluid flow from the first fluid reservoir 12. As fluid 16 is released or flows into the patient conduit 50, the height of the second fluid reservoir 42 is returned to a position lower than the height of the vent 74 thereby permitting the vent 74 to release positive pressure within the drip chamber 40. As the pressure within the drip chamber 40 equalizes, fluid flow from the first fluid reservoir 12 resumes.

In some embodiments, the vent 74 further comprises a filter (not shown) that is configured to entrap or render harmless aerosolized, hazardous gas 24 within the drip chamber. In other embodiments, the vent 74 further comprises a conduit (not shown) that vents hazardous gas 24 from the drip chamber 40 directly into the first fluid reservoir 12. For example, in some embodiments the coupling assembly 20 may further include a parallel air channel (not shown) that is coupled to first fluid reservoir 12. Further, in some embodiments the vent 74 comprises a conduit (not shown) that vents hazardous gas 24 from the drip chamber 40 into a chemical hood (not shown) or another container to prevent undesired exposure of the hazardous gas 24 to the environment.

Upon contact of the fluid 160 with the vent membrane 58, the flow of the fluid 160 is halted thereby terminating fluid flow through the membrane 66. Prior to removing the vent membrane 58, the roller clamp 52 may be so as to retain the primed state of the patient conduit 50. This self-priming configuration provides efficient purging of air within the system without the need to manually displace air bubbles via flicking or other manual manipulation of the components of the system 10.

Figure 1C:
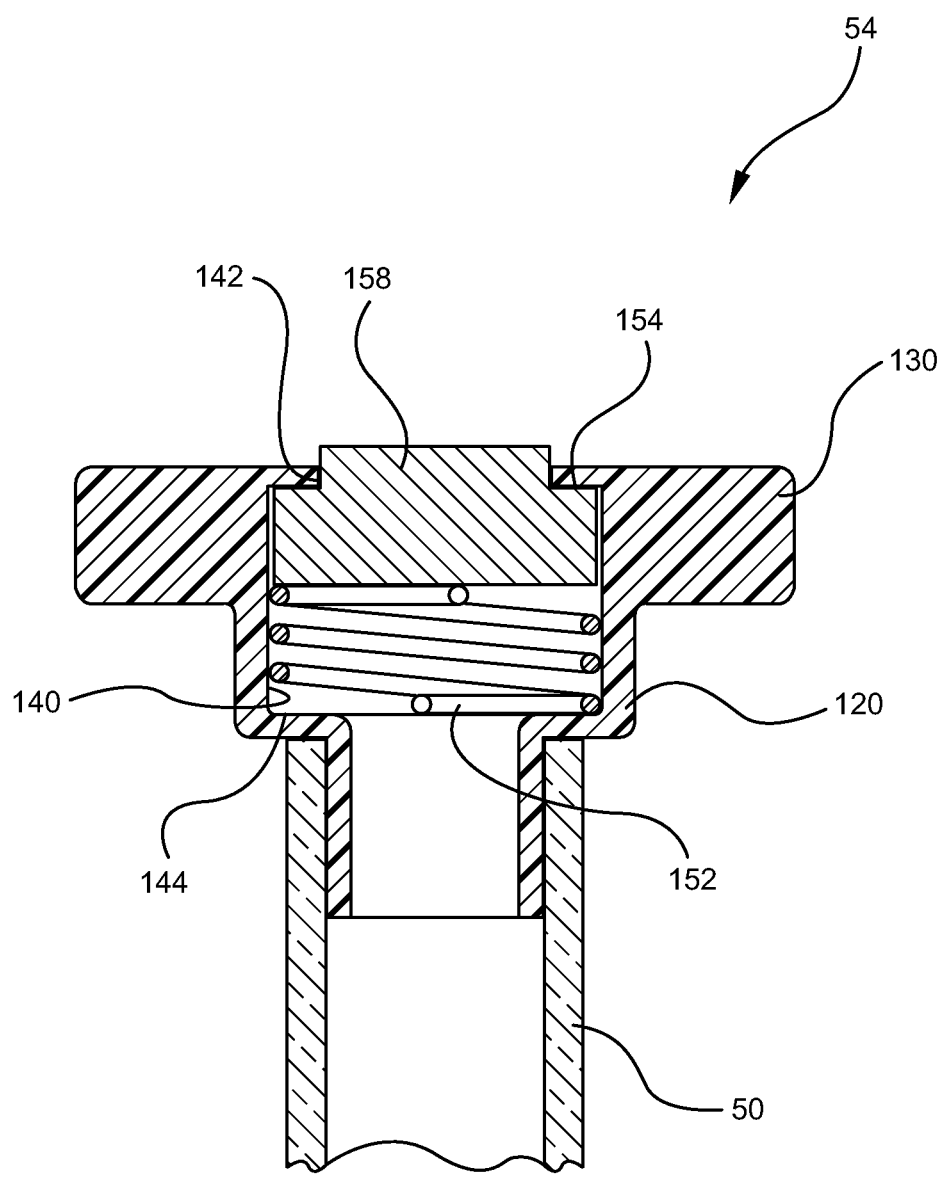
FIG. 1C is a cross-section view of a terminal end of an IV set incorporating a vent membrane in accordance with a representative embodiment of the present invention.

In some embodiments, end 54 is configured such that upon coupling a luer device to end 54, vent membrane 58 is automatically defeated thereby resuming fluid flow through the conduit. With reference to FIG. 1C, a representative embodiment of a luer-activated vent membrane 158 is shown. One of skill in the art will appreciate that this embodiment represents only one of many methods and designs by which a luer actuated membrane may be provided. In general, end 54 comprises a plug 120 insertedly coupled into an end of patient conduit 50. An opening between plug 120 and conduit 50 provides for fluid communication between the two components. A flanged portion 130 of plug 120 is provided as a means for securing a coupler (not shown) associated with a luer device (not shown). An internal cavity 140 of plug 120 is configured to house vent membrane 158 and biasing means 152. In some embodiments, biasing means 152 comprises a coiled spring or a perforated elastomeric material. In other embodiments, a portion of vent membrane 158 is modified to provide a biasing function.

In some embodiments, a first end portion of cavity 140 comprises a retaining ridge 142 having an inner diameter that is smaller than an outer diameter of the vent membrane 158. Cavity 140 further comprises a second end portion having a stepped surface 144 for supporting biasing means 152. Thus, membrane 158 and biasing means 152 are interposedly positioned between retaining ridge 142 and stepped surface 144 within cavity 140. As configured, biasing means 152 positions membrane 158 against retaining ridge 142 so that a seal 154 is formed between membrane 158 and the retaining ridge 142. Thus, during the priming process air within the system 10 is vented from the system 10 through membrane 158, however the physical properties of membrane 158 and/or the seal 154 prevent passage of fluids.

Figure 1D:
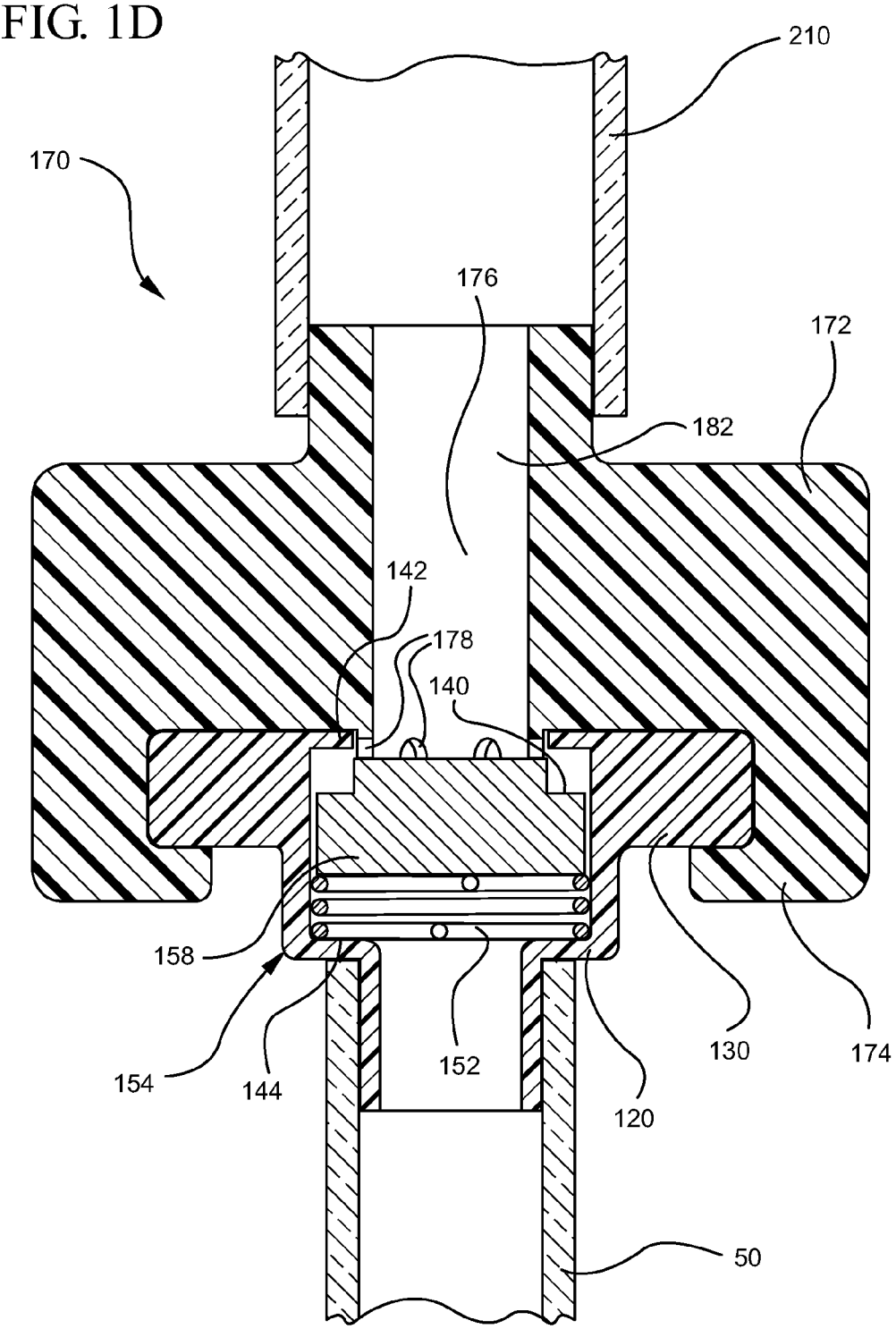
FIG. 1D is a cross-section view of a terminal end of an IV set incorporating a vent membrane as coupled to a luer device in accordance with a representative embodiment of the present invention.

With reference to FIG. 1D, seal 154 is defeated upon coupling luer device 170 to end 54. Luer device 170 may include any device having a configuration capable of actuating membrane 158. In some embodiments, luer device 170 comprises a body 172 having a feature 174 for coupling to plug 120. Luer device 170 further comprises an internal cavity 182 in fluid communication with a downstream device, such as a catheter or catheter tubing 210. Luer device 170 further comprises a probe portion 176 configured to partially insert within plug 120 and contact membrane 158. Upon contact between probe portion 176 and membrane 158, membrane 158 is repositioned such that seal 154 is defeated. A plurality of holes or ports 178 located in probe portion 176 provides fluid communication between plug 120 and internal cavity 182 of the luer device 170 such that fluid is permitted to flow into catheter tubing 210.

Referring now to FIG. 3, following priming of the drip chamber 40 and patient conduit 50, the spike 30 of the coupling assembly 20 is coupled to a first fluid reservoir 12. In some embodiments, the first fluid reservoir 12 is an IV bag which contains a hazardous chemical or drug 16. In other embodiments the first fluid reservoir 12 is an IV bottle or other similar reservoir device. The fluid reservoir 12 generally includes a septum 36, or puncturable membrane through which the spike 30 is compatibly inserted. Once inserted, the roller clamp 52 is released and the hazardous drug 16 is permitted to flow through the coupling assembly 20, into the drip chamber 40 and into the patient conduit 50, as illustrated in FIG. 4. For those embodiments incorporating a rigid or semi-rigid IV bottle, a portion of the drip chamber 40 may further include a vent 74. In some embodiments, the vent 74 includes a filter designed to minimize potential for passing of aerosolized or gas 24 form of hazardous drugs within the IV delivery system 10, as the hazardous drug 16 moves through the system 10.

Referring now to FIG. 4, following infusion of the hazardous drug 16, a flushing fluid 160 is added to the drip chamber 40 via the self-sealing priming/flushing port 44. In some embodiments, the flushing fluid 160 is identical to the priming solution 160. In other embodiments, the flushing fluid 160 is a secondary, non-hazardous drug. The flushing fluid 160 pushes the remaining hazardous drug 16 into the patient thereby ensuring complete infusion of the medicament 16. Infusion of the flushing fluid 160 further acts to clean or decontaminate the catheter 102 portion of the IV delivery system 10 from residual hazardous drug 16. Once a sufficient volume of the flushing fluid 160 has been infused, the catheter 102 may be safely removed from the insertion site 106 without exposing the technician or patient 100 to the hazardous drug 16.

Figure 5:
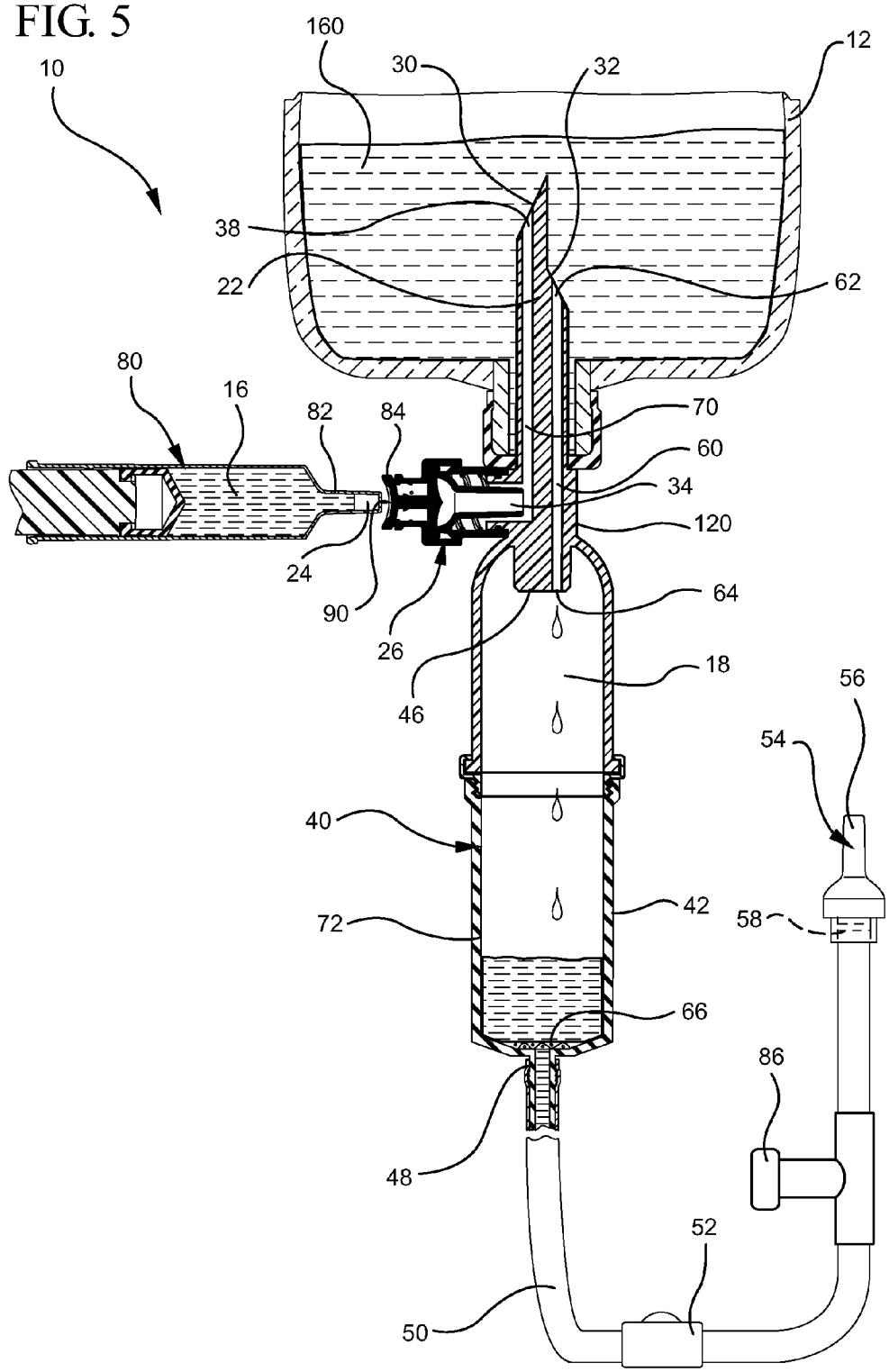
FIG. 5 is a cross-section view of an implementation of an IV set of the present invention, wherein the IV set is coupled to an IV bag and includes an access port.

In some embodiments of the present invention, the IV delivery system 10 includes a coupling assembly 120 having multiple fluid channels 60 and 70, as shown in FIG. 5. As previously discussed, the first fluid channel 60 provides a fluid pathway between a coupled fluid reservoir 12 and the drip chamber 40 of the IV delivery system 10. In some embodiments, the first fluid channel 60 further comprises a second fluid channel 70 providing a fluid pathway between a self-sealing access port 26 and the coupled fluid reservoir 12. The second fluid channel 70 includes an input 34 and an output 38, the input 34 being coupled to an inner portion of the access port 26, and the output 38 being in fluid communication with the fluid 160 of the fluid reservoir 12. In some embodiments, the first fluid channel 60 and the second fluid channel 70 share a common, dividing wall 22 running the length of both fluid channels 60 and 70. In some embodiments the second fluid channel 70 is a tube (not shown) wherein the walls of the tube divide the first fluid channel 60 from the second fluid channel 70.

In some embodiments, the second fluid channel 70 further includes an access port 26. The access port 26 is coupled to an outer surface of the coupling assembly 120 and is in fluid communication with the second fluid channel 70. The access port 26 is designed to compatibly receive a syringe 80 or other delivery device configured to deliver a hazardous drug 16 to the fluid reservoir 12 via the second fluid channel 70. In some embodiments, the access port 26 is designed to receive and irreversibly retain a syringe 80. In other embodiments, the access port 26 comprises a set of threads (not shown) configured to receive a compatible set of threads (not shown) located on a portion of the syringe 80. In other embodiments the access port 26 and the syringe 80 are coupled together via a luer-lock coupling assembly.

The access port 26 generally includes an opening 90 for receiving a tip portion 82 of the syringe 80. The access port 26 further includes a valve or split septum 84 which is opened by inserting the tip 82 into the opening 90. Prior to insertion of the tip portion 82, the septum 84 is biased into a closed, sealed configuration thereby preventing leakage of the priming fluid 160 into the second fluid channel 70 via the output 38. In some embodiments, the carrier fluid is the priming fluid 160 of the fluid reservoir 12. For those embodiments where the tip portion 82 and the opening 90 are reversibly coupled or reversibly interlocked, upon removal of the tip 82 from the opening 90, the septum 84 resumes its closed, sealed configuration thereby preventing leakage of fluid from the second fluid channel 70.

In some embodiments of the present invention, the drip chamber 40 and patient conduit 50 are primed with a priming fluid 160 prior to injection of the hazardous drug 16 via the access port 26. The process of priming the system 10 requires that a spike portion 30 of the coupling assembly 120 first be inserted into the first fluid reservoir 12 containing the priming fluid 160. For those embodiments that are configured in a self-priming configuration, the priming fluid 160 of the first fluid reservoir 12 automatically flows into the drip chamber 40 and the patient conduit 50 thereby providing a second fluid reservoir 42 as well as displacing air within the conduit 50.

In some embodiments, the system 10 is configured to exclude the vent membrane 58, and comprises only a membrane 66. For these embodiments, the process of priming the system 10 comprises first occluding the patient conduit 50 via a roller clamp 52 or similar clamping device. Following occlusion, the spike portion 30 of the coupling assembly 120 is inserted into the first fluid reservoir 12. A flexible portion 72 of the drip chamber 40 is then compressed or otherwise manipulated to draw fluid 160 into the drip chamber 40 via the first fluid channel 60, as is conventional. Once a second fluid reservoir 42 is formed, the roller clamp 52 is released and the priming fluid 160 resumes flow from the first reservoir 12 and through the patient conduit 50 to purge air within the conduit 50.

In other embodiments, the system 10 is configured to exclude the membrane 66, and comprises only a vent membrane 58. For these embodiments, the process of priming the system 10 comprises inserting the spike portion 30 of the coupling assembly 120 into the first fluid reservoir 12 prior to occluding the patient conduit 50 via a roller clamp 52. The priming fluid 160 freely flows from the first fluid reservoir 12 into the drip chamber 40 and the patient conduit 50. Once the priming fluid 160 reaches the vent membrane 58, fluid flow ceases and the patient conduit 50 is occluded via the roller clamp 52. At this point, the system 10 is completely primed with the priming fluid 160 resulting in complete displacement and purging of air within the patient conduit 50. In some embodiments, the dust cap 56 and adjoining vent membrane 58 are removed from the terminal end 54 of the patient conduit 50, and the patient conduit 50 is coupled to a secondary patient conduit (not shown) or coupled to an intravenous catheter 102, as shown in FIG. 6.

Figure 6:
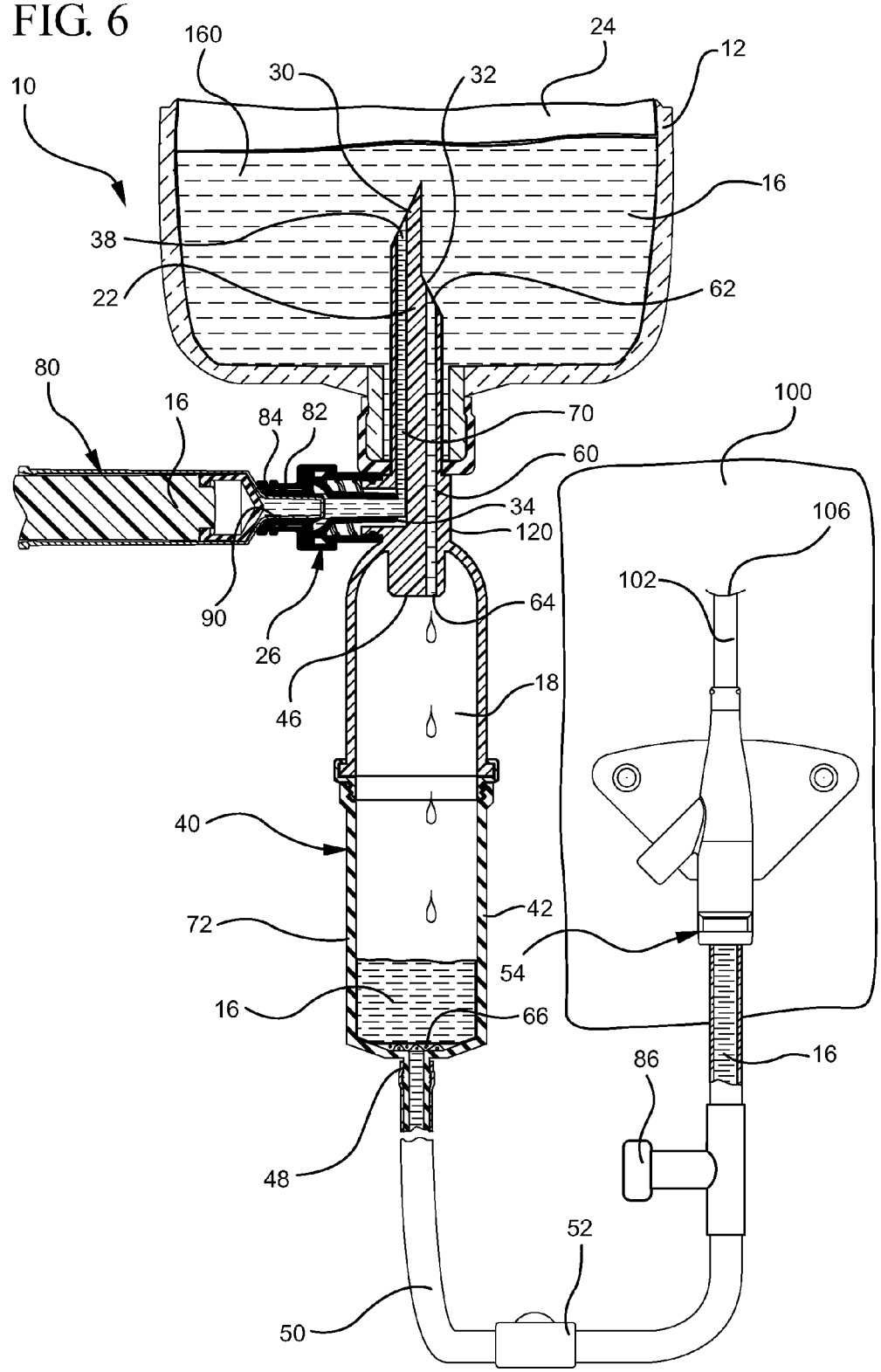
FIG. 6 is a cross-section view of an implementation of an IV set of the present invention wherein the IV bag is injected with a hazardous drug via an access port.

Referring now to FIG. 6, a hazardous drug 16 is injected into the first fluid reservoir 12 via the access port 26 and a syringe 80. In some embodiments, a tip portion 82 of the syringe 80 is inserted into an opening 90 of the access port 26, such that the tip portion 82 biases the septum 84 into an opened position. The syringe 80 is then actuated to supply the hazardous drug 16 to the first fluid reservoir 12. The hazardous drug 16 and the priming fluid 160 of the first fluid reservoir are mixed to provide a desired concentration of the hazardous drug 16 in the priming fluid 160. The roller clamp 52 is then released to resume flow of the fluid 16 through the system 10 and into the patient 100 via the coupled catheter 102.

In some embodiments, the patient conduit 50 further includes a flush port 86. The flush port 86 generally comprises an adapter coupled to an outer surface of the patient conduit 50. The flush port 86 includes an opening 88 configured to compatibly receive a tip portion 182 of a syringe 180. In some embodiments, the opening 88 further comprises a septum 84 that may be biased to an opened position by introduction of the syringe tip portion 182 in the opening 88. In other embodiments, the opening 88 further comprises a puncturable membrane that is defeated to an opened position by introduction of the syringe tip 182 into the opening 88. Other embodiments of the flush port 86 include a valve or other device that permits a syringe 180 to fluidly access the patient conduit 50, as shown in FIG. 7.

Figure 7:
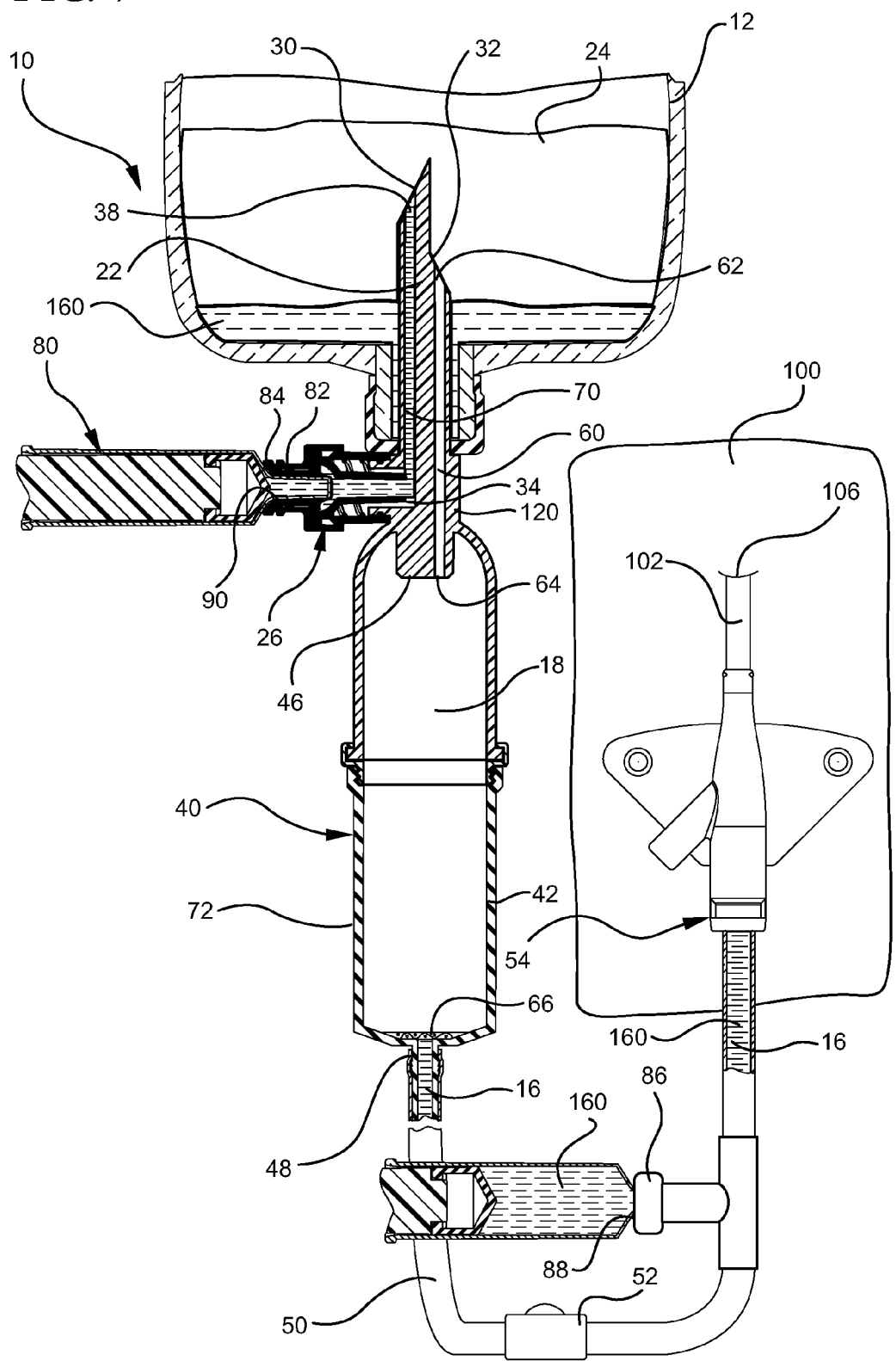
FIG. 7 is a cross-section view of an implementation of an IV set of the present invention wherein a portion of a patient conduit is flushed with a priming fluid via a flush port.

Referring now to FIG. 7, the IV system is shown following infusion of the hazardous drug 16. In some embodiments, a hazardous vapor 24 and unused hazardous drug remains in the first fluid reservoir 12 following the infusion procedure. In other embodiments, the syringe 80 and the access port 26 are irreversibly interlocked to prevent removal of the syringe 80 resulting in unwanted exposure to the remaining hazardous drug 16. For those embodiments comprising an anti-run dry membrane 66, the hazardous drug 16 completely empties from the drip chamber 40, but does not drain past the membrane 66. Rather, the hazardous drug 16 remains within the membrane 66 and prevents introduction of air into the patient conduit 50. As a result, flow of the hazardous drug 16 through the patient conduit 50 ceases resulting in the patient conduit 50 being filled with hazardous drug 16. Additionally, the inserted portion of the catheter 102 remains contaminated with the hazardous drug 16. Thus, in some embodiments an outer surface of the patient conduit 50 is modified to include a flush port 86. The flush port 86 is configured to compatibly receive a syringe 180 containing a priming or flushing fluid 160 to rinse the catheter portion 102 of the IV delivery system 10 prior to removal of the catheter 102 from the patient 100.

The process for flushing the patient conduit 50 via the flushing port 86 first requires that the patient conduit 50 be occluded via the roller clamp 52. In some embodiments, the roller clamp 52 is interposedly positioned over the outer surface of the patient conduit 50 between the drip chamber 40 and the flushing port 86. Once the patient conduit 50 is occluded, the syringe 180 is inserted into the opening 88 of the flushing port 86 to provide fluid communication between the syringe 180 and the fluid 16 within the patient conduit 50. The syringe 180 is then actuated to inject and infuse the flushing fluid 160 into the patient via the patient conduit 50 and the catheter 102. In the process of infusing the flushing fluid 160, the downstream portion of the patient conduit 50, as well as the inserted portion of the catheter 102 is thoroughly rinsed with the flushing fluid 160. As such, the inserted portion of the catheter 102 is decontaminated from the hazardous drug 16 and may be safely removed without exposure to the hazardous drug 16. The IV delivery system 10, coupled syringes 80 and 180, and remaining hazardous drug 16 may then be safely disposed without topical or inhaled exposure to the hazardous drug 16.

Various features of the present invention may be used in combination to provide an IV delivery system 10 to safely administer a hazardous drug 16 to a patient 100. For example, with reference to FIG. 8, an IV delivery system 10 is provided incorporating both a priming/flushing port 44 and an access port 26. In some embodiments, a coupling assembly 120 is provided having a first fluid channel 60 and a second fluid channel 70. The first fluid channel 60 provides fluid communication between the coupling assembly 120 and an attached drip chamber 40. In some embodiments, a spike portion 30 of the coupling assembly 120 is inserted into a fluid reservoir 12, such as an IV bag or IV bottle. As such, the first fluid channel 60 of the coupling assembly 120 provides a conduit to permit flow of a fluid 160 from the fluid reservoir 12 to the drip chamber 40, as shown in FIG. 9.

Figure 10:
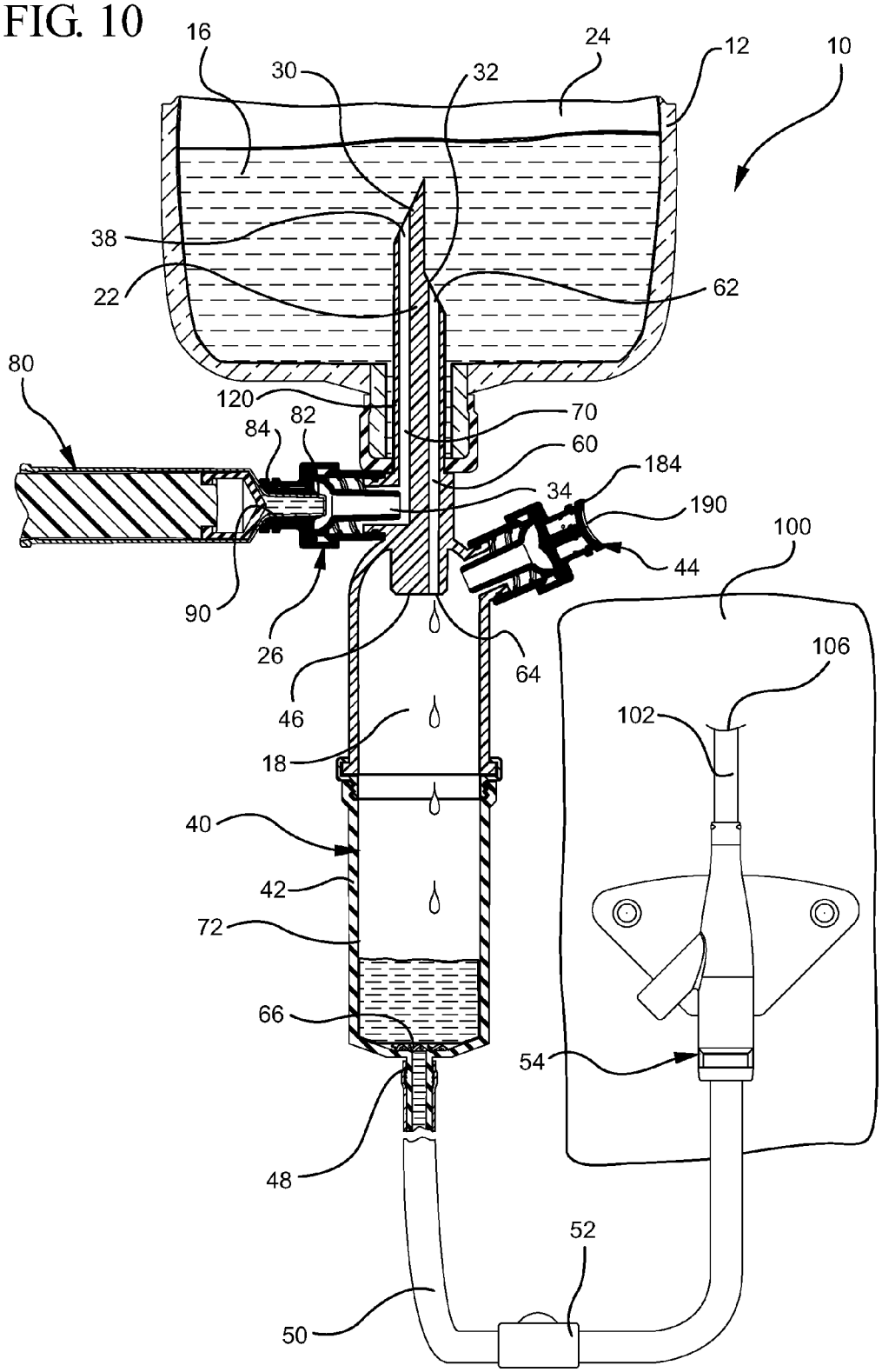
FIG. 10 is a cross-section view of an implementation of an IV set of the present invention following injection of a hazardous drug into an IV bag via an access port.

The second fluid channel 70 forms a portion of the coupling assembly 120 and generally runs parallel to the first fluid 60, as previously discussed. The second fluid channel 70 further comprises an access port 26 whereby a fluid 16 is externally injected into the second fluid channel 70. In some embodiments, an opening or output 38 of the second fluid channel is located on the spike portion 30 of the coupling assembly 120. Thus, when the spike portion 30 of the coupling assembly 120 is inserted into a first fluid reservoir 12, a fluid 16 may be injected into the fluid reservoir 12 via the second fluid channel 70, as shown in FIG. 10. In some embodiments, an opening 90 of the access port 26 is configured to compatibly receive a syringe 80 or other similar fluid delivering apparatus. In other embodiments, the opening 90 is modified to include a feature for reversibly interlocking the syringe 80 and the access port 26. Further, in some embodiments the opening 90 is modified to include a feature or features for receiving and permanently interlocking the syringe 80 and the access port 26.

Figure 8:
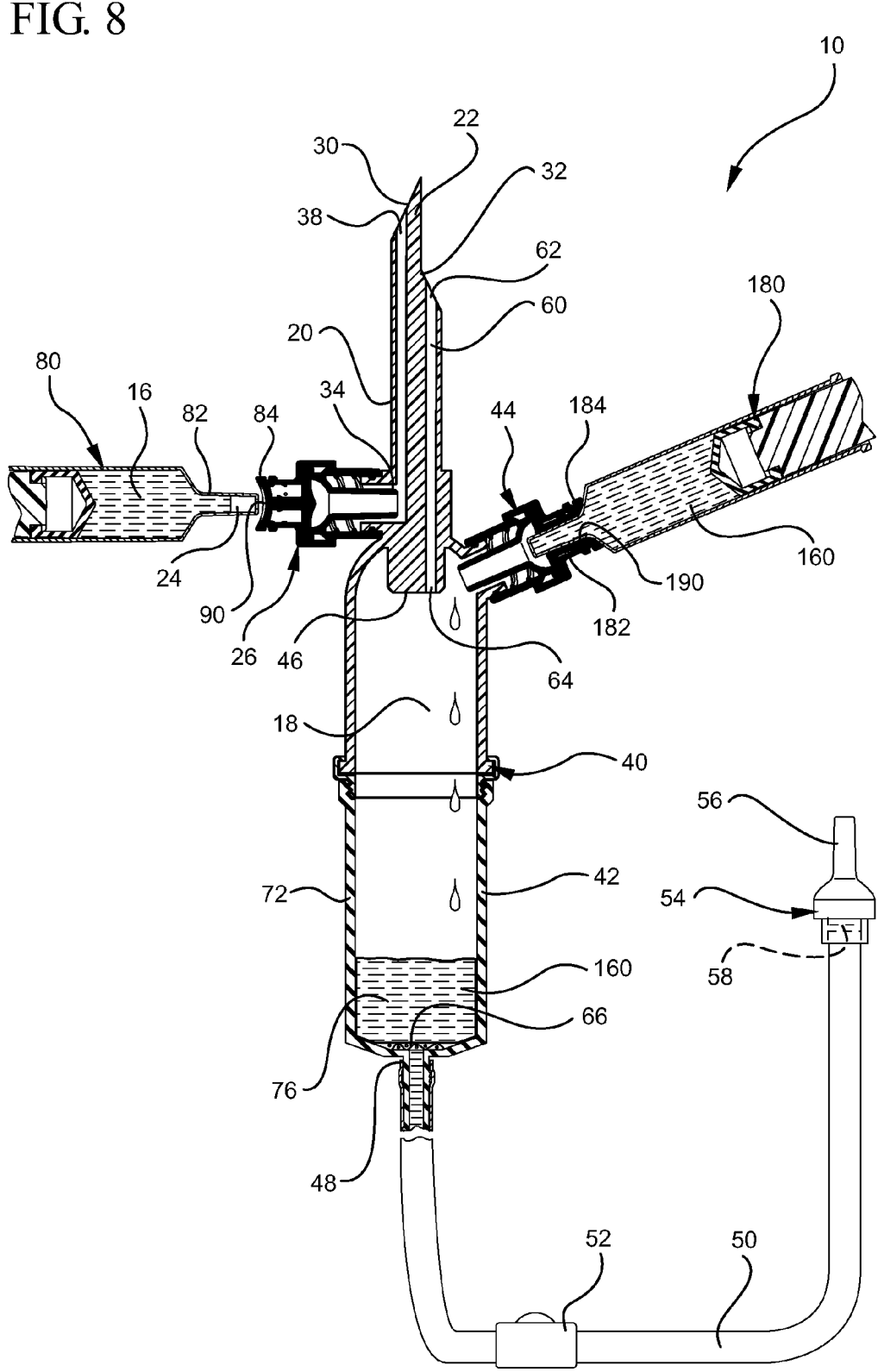
FIG. 8 is a cross-section view of an implementation of an IV set of the present invention having a priming port and an access port.

In some embodiments, a portion of the drip chamber 40 is modified to include a priming/flushing port 44. The priming/flushing port 44 provides direct access to the drip chamber 40, as previously discussed in connection with FIGS. 1-4 above. Thus, in some embodiments the drip chamber 40 and the patient conduit 50 are primed with a priming solution 160 via a syringe 180 and the priming/flushing port 44, as shown in FIG. 8. In other embodiments, the drip chamber 40 and patient conduit 50 are primed by inserting the spike portion 30 of the coupling assembly 120 into a first fluid reservoir 12 containing a priming fluid 160, as shown in FIG. 9. For those embodiments implementing a vent membrane 58, the priming fluid 160 automatically flows into the drip chamber 40 and through the patient conduit 50 displacing air present therein.

Figure 9:
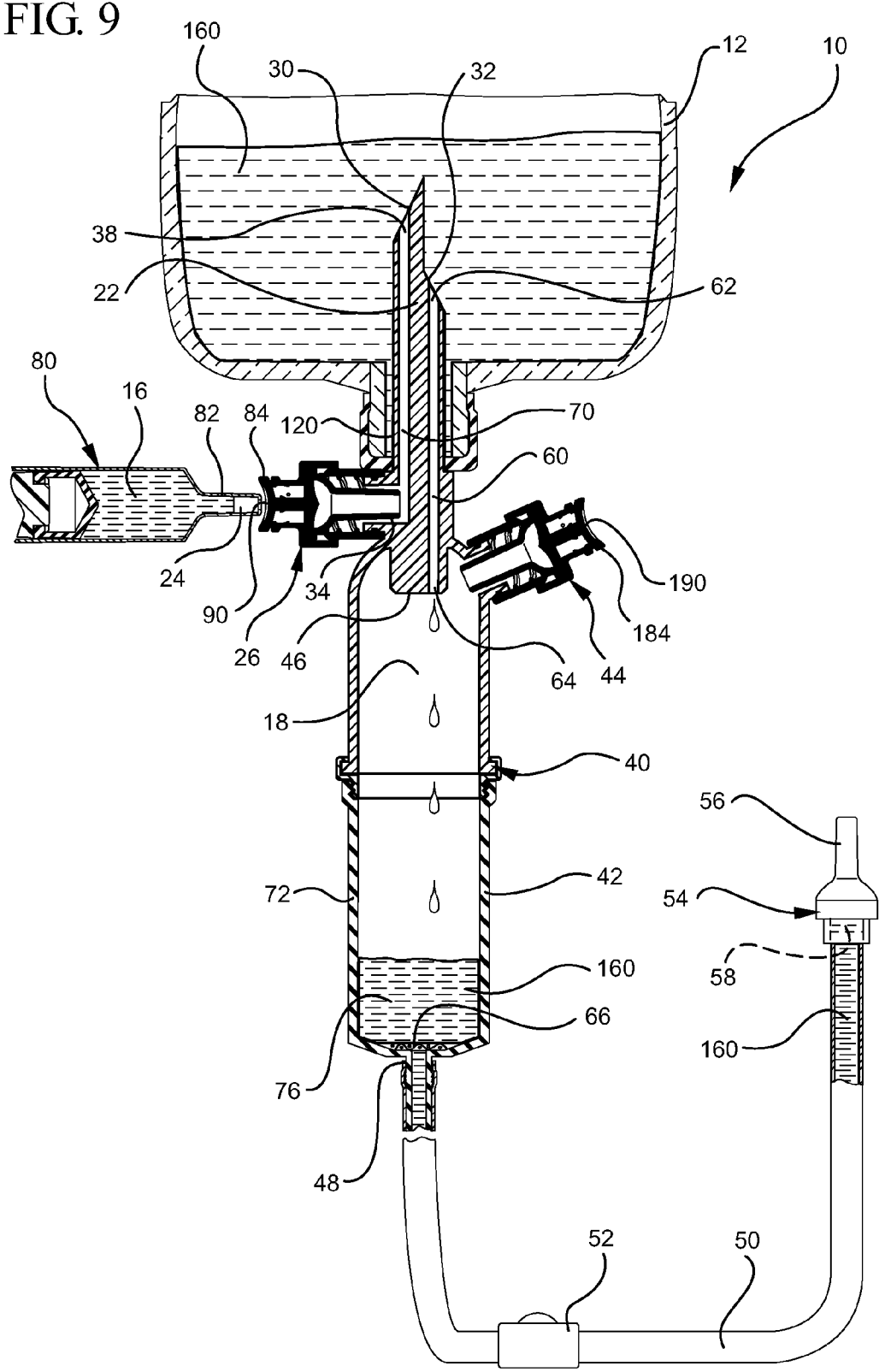
FIG. 9 is a cross-section view of an implementation of an IV set of the present invention in a primed state.

Following the priming procedures of FIGS. 8 and 9, the patient conduit 50 is occluded with a roller clamp 52, and a hazardous drug 16 is introduced into the first fluid reservoir 12 via the second fluid channel 70 and access port 26, as shown in FIG. 10. Generally, a tip portion of the syringe 80 is inserted into the opening 90 of the access port 26 to bias open the septum 84 and initiate fluid communication between the syringe 80 and the second fluid channel 70. The highly concentrated hazardous drug 16 within the syringe 80 is then injected into the first fluid reservoir 21 via the second fluid channel 70. The hazardous drug 16 is then mixed with the priming fluid 160 of the first fluid reservoir 12 to provide a solution of hazardous drug 16 at a desired concentration. The roller clamp 52 is then released to allow flow of the diluted hazardous drug 16 into the drip chamber 40 and patient conduit 50. In some embodiments, the vent membrane 58 and dust cap 56 are replaced with an intravenous catheter 102 to permit intravenous infusion of the hazardous drug 16 into a patient 100.

Figure 11:
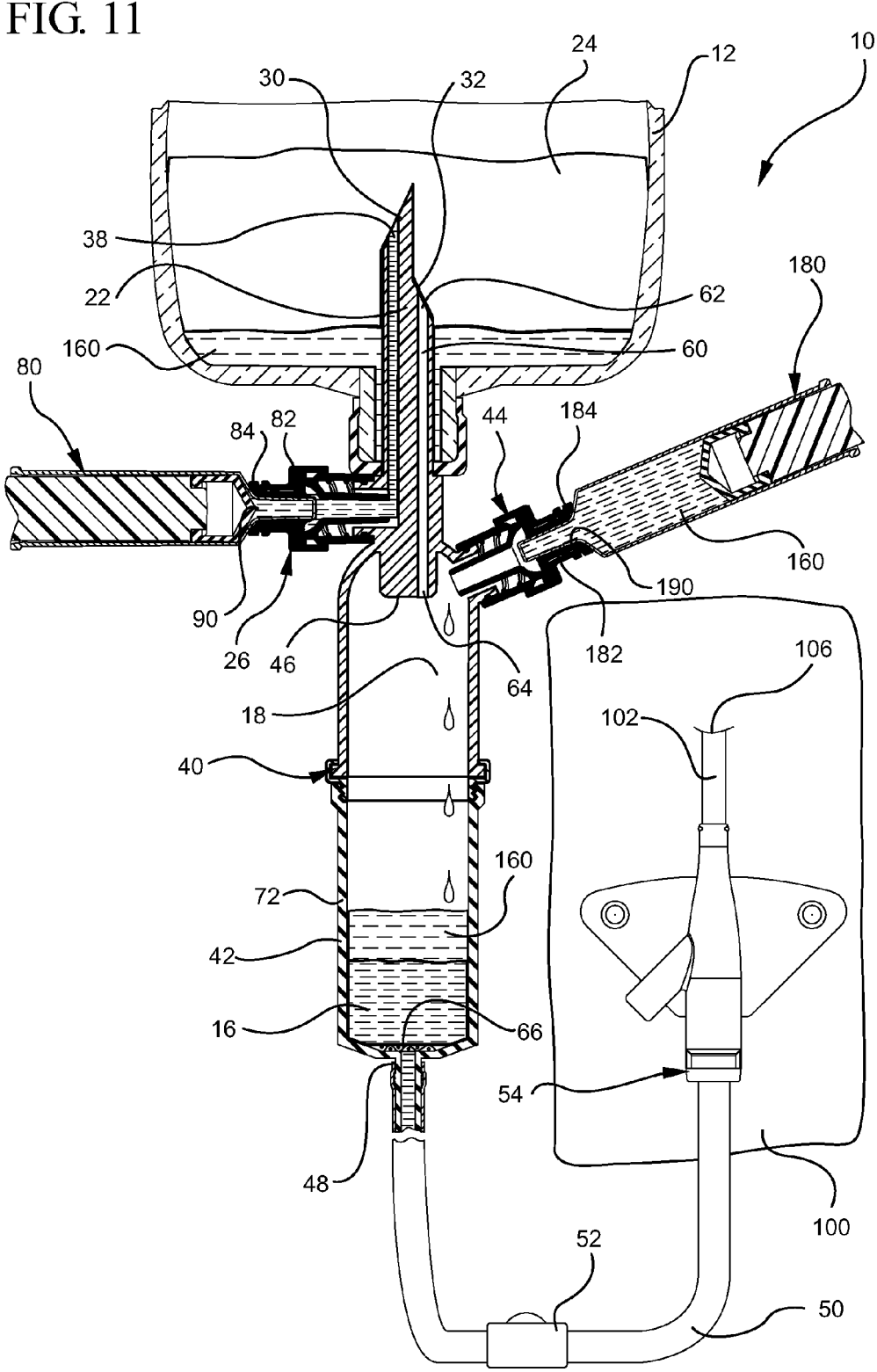
FIG. 11 is a cross-section view of an implementation of an IV set of the present invention following infusion of a hazardous drug into a patient, wherein the IV set is being flushed with a priming fluid via a priming port.

Following the infusion procedure of FIG. 10, the remaining hazardous drug 16 within the drip chamber 40 and patient conduit 50 is flushed into the patient 100 by adding a flushing fluid 160 to the drip chamber via the priming/flushing port 44, as shown in FIG. 11. In some embodiments, the flushing fluid 160 is the same as the priming fluid 160 in FIG. 9. In other embodiments, the flushing fluid 160 is a secondary, non-hazardous drug. As the flushing fluid 160 flows through the drip chamber 40, patient conduit 50, and catheter 102, residual hazardous drug 16 is infused into the patient 100. Additionally, the components 40, 50 and 102 are decontaminated from the hazardous drug 16 thereby permitting safe removal of the catheter 102 from the patient 100 without the possibility of topical or inhaled exposure to the drug 16 or hazardous vapor 24. Following removal of the catheter 102, the IV delivery system 10, residual drug 16, and coupled syringes 80 and 180 are appropriately disposed.

In some embodiments of the present invention, the IV delivery includes neither an anti-run dry membrane 66 nor a vent membrane 58. For these embodiments, a clinician initiates flow from the fluid reservoir 12 by squeezing a flexible portion 72 of the drip chamber 40, as is conventional. In other embodiments, the drip chamber 40 and patient conduit 50 are pre-primed from the manufacturer with a priming fluid 160. Prior to attaching the coupling assembly 20 or 120 to the first fluid reservoir 12, the patient conduit 50 is occluded via a clamp 52. A hazardous drug 16 is then injected into the fluid reservoir 12 via the access port 26, and flow is initiated through the system 10 by releasing the clamp 52. In some embodiments, the clamp 12 is selectively adjustable to enable a desired flow rate through the patient conduit 50. In other embodiments, trace drug 16 remaining in the second fluid channel 70 is flushed into the first fluid reservoir 12 by repeatedly actuating the syringe 80.

A common practice is to pre-inject a fluid reservoir 12 with a hazardous drug 16 prior to delivery to a clinician. Pre-injecting the hazardous drug 16 is commonly done by a pharmacist or other technician under a chemical hood or in a well ventilated area. Pre-injection eliminates the need for a clinician to handle the highly concentrated hazardous drug, and further ensures proper dosage. The pre-injected reservoir is delivered to the clinician for administration to the patient. Some embodiments of the present invention are used in conjunction with pre-injected reservoirs, as well as with multiple or serially connected fluid reservoirs.

Figure 12:
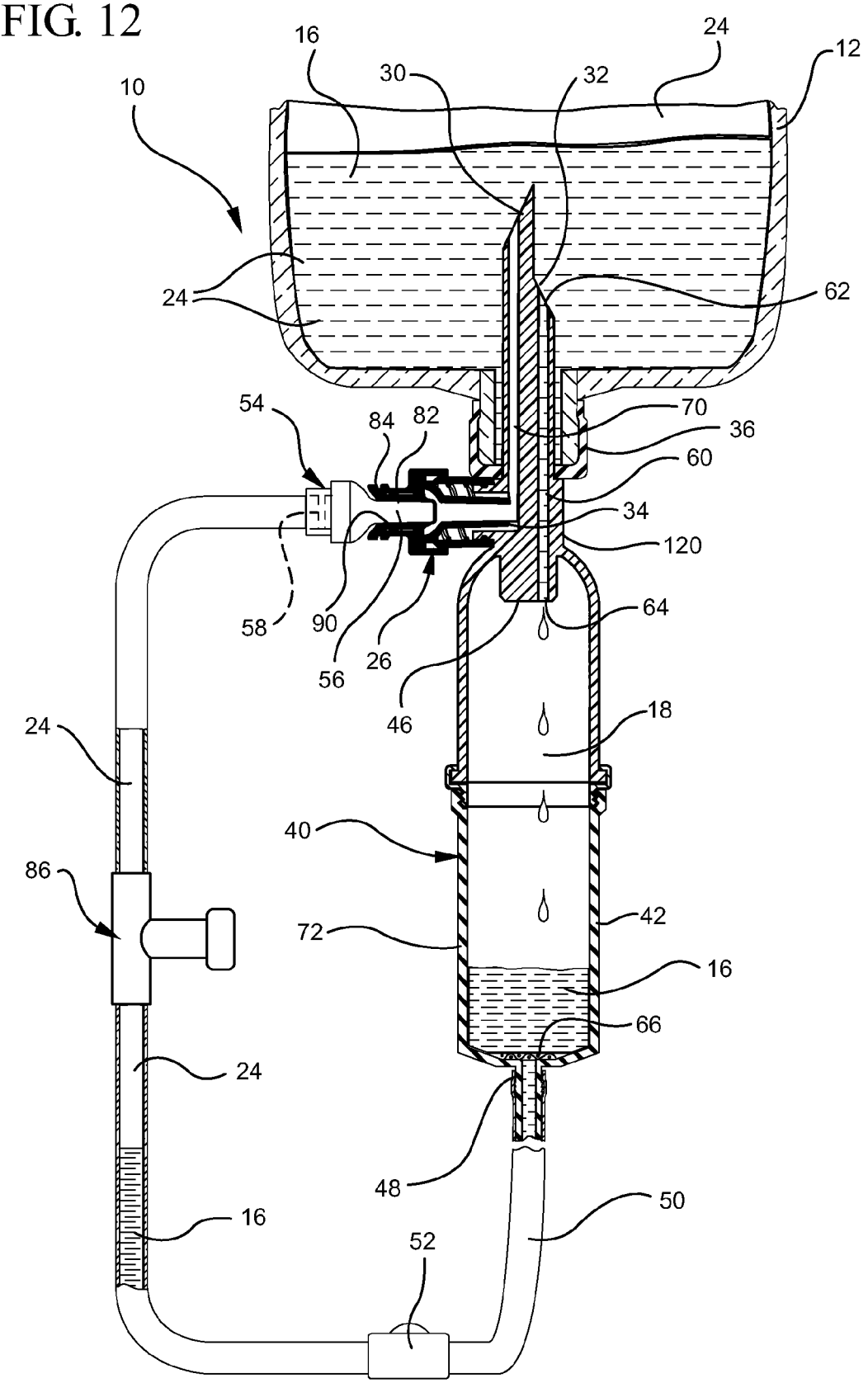
FIG. 12 is a cross-section view of an implementation of an IV set of the present invention in a closed vent configuration.

In some embodiments, the second fluid channel 70 is used to vent a hazardous vapor 24 into the first fluid reservoir 12, as shown in FIG. 12. For example, in some embodiments air within the patient conduit 50 is purged by priming the conduit 50 directly with the hazardous drug 16 from a pre-injected fluid reservoir 12. As the hazardous drug 16 exits the drip chamber 40 and proceeds through the patient conduit 50, hazardous vapor 24 from the hazardous drug 16 is pushed through conduit 50. While the flow restriction device 58 prevents the liquid hazardous drug 16 from exiting the conduit 16, the device 58 is dually designed to readily permit passage of the hazardous vapor 24. Thus, during the priming process the clinician may be undesirably exposed to the hazardous vapor 24.

Therefore, in some embodiments of the present invention, the terminal end 54 of the patient conduit 50 is compatibly inserted into the access port 26 prior to priming the IV set 10 with the hazardous drug 16. Once the terminal end is coupled to the access port 26, the roller clamp 52 is released to initiate flow of the hazardous drug 16 into the drip chamber 40. As the hazardous drug 16 moves through the patient conduit 50, hazardous vapor 24 is displaced from the conduit 50 and into the fluid reservoir 12 via the second fluid channel 70. Thus, the patient conduit 50 is purged of trapped air, and hazardous vapor 24 from the hazardous drug 16 is gassed into the fluid reservoir 12 and contained in the system 10. This priming process ensures thorough priming while preventing unsafe exposure of the hazardous drug 16 and vapors 24 to the clinician.

Following the priming process, the conduit 50 is occluded again occluded with the roller clamp 52 and the terminal end 54 is removed from the access port 26. The clinician may then remove the dust cap 56 and vent membrane 58 to enable attachment of the conduit 50 to a patient 100 via a catheter 102. In some embodiments, the dust cap 56 further comprises a valve device whereby a catheter 102 is directly and fluidly coupled to the patient conduit 50 without removing the dust cap 56 or vent membrane 58. In other embodiments, the vent membrane 58 is capable of being punctured by a portion of an IV catheter 102, whereby the IV catheter 102 is directly and fluidly coupled to the patient conduit 50 without removing the flow control device 58. As such, the clinician may safely attach the patient conduit 50 to the patient 100 without being exposed to the hazardous drug 16 within the patient conduit 50. Further, in some embodiments the patient conduit 50 further comprises a flush port 86 whereby the terminal end 54 and coupled catheter 102 of the system 10 are flushed with a flushing fluid 116 prior to removal from the patient 100.

Figure 13:
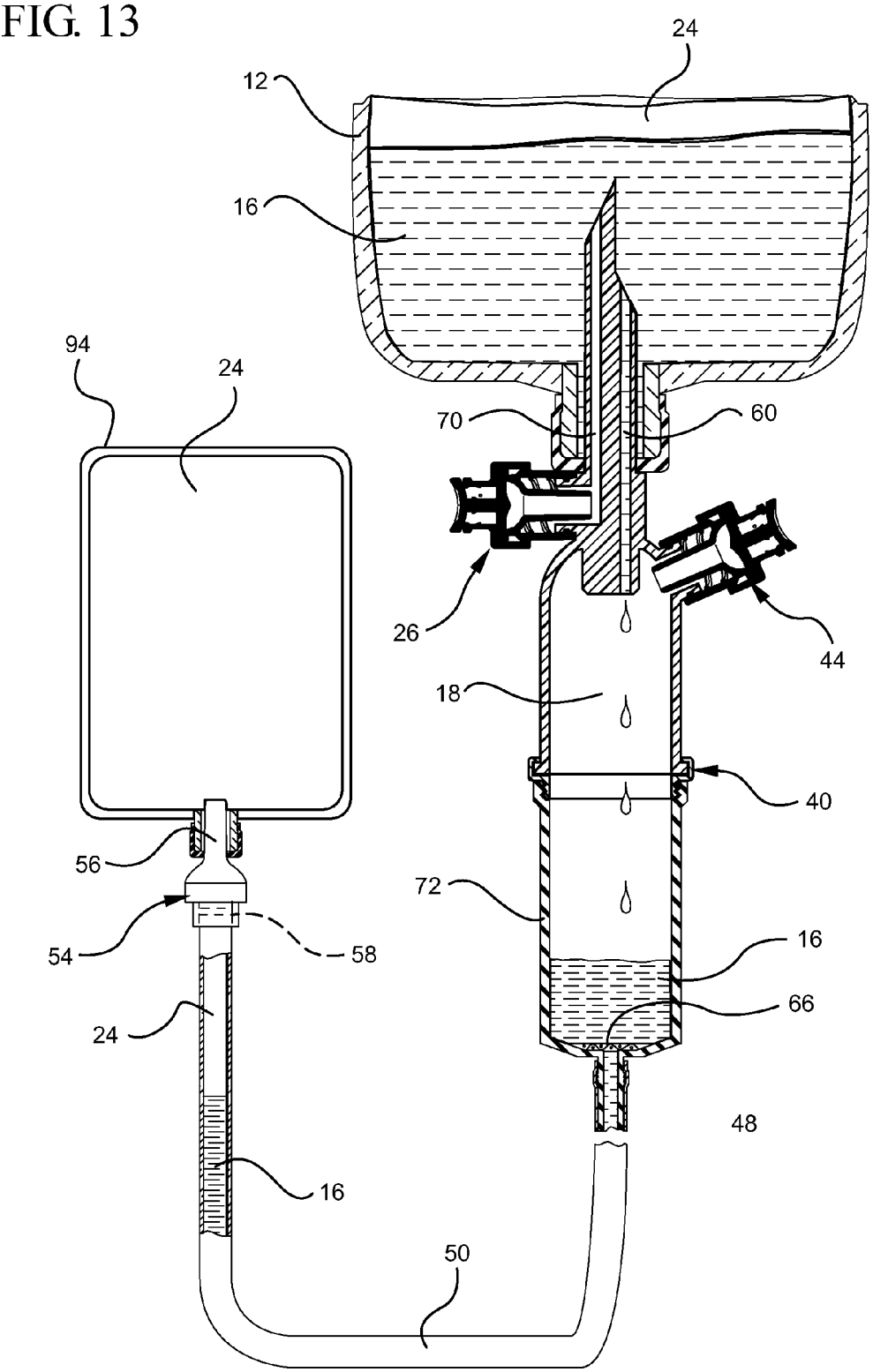
FIG. 13 is a cross-section view of an implementation of an IV set of the present invention shown venting a hazardous vapor into a detached container.

Referring now to FIG. 13, an implementation of the present invention is shown during the process of priming the patient conduit 50 with a hazardous drug 16. In some embodiments, the terminal end 54 of the patient conduit 50 is coupled to a container 94 configured to receive and contain the hazardous vapor 24 displaced from the conduit 50 during the priming process. The container 94 may include any device or system capable of preventing undesirable exposure to the hazardous vapor 24. For example, in some embodiments the container 94 is a tank. In other embodiments, the container 94 is a ventilation hood, or a filtration system. Still, in other embodiments container 94 is a disposable bag or balloon.

In some embodiments container 94 further comprises neutralizing or catalyzing agents that sequester or otherwise interact with the vapor 24 to reduce its hazardousness. In other embodiments, the cap 56 or vent membrane 58 are further modified to permit attachment of the terminal end to a patient 100 via a catheter 100, or other device without exposing the clinician to hazardous vapor 24 or hazardous drug 16 within the conduit 50. Still further, some drip chambers 40 of the present invention include a priming/flushing port 44 whereby hazardous drug 16 within the patient conduit 50 and coupled catheter 102 is flushed prior to removal of the same from the patient 100 following the infusion procedure.

Figure 14:
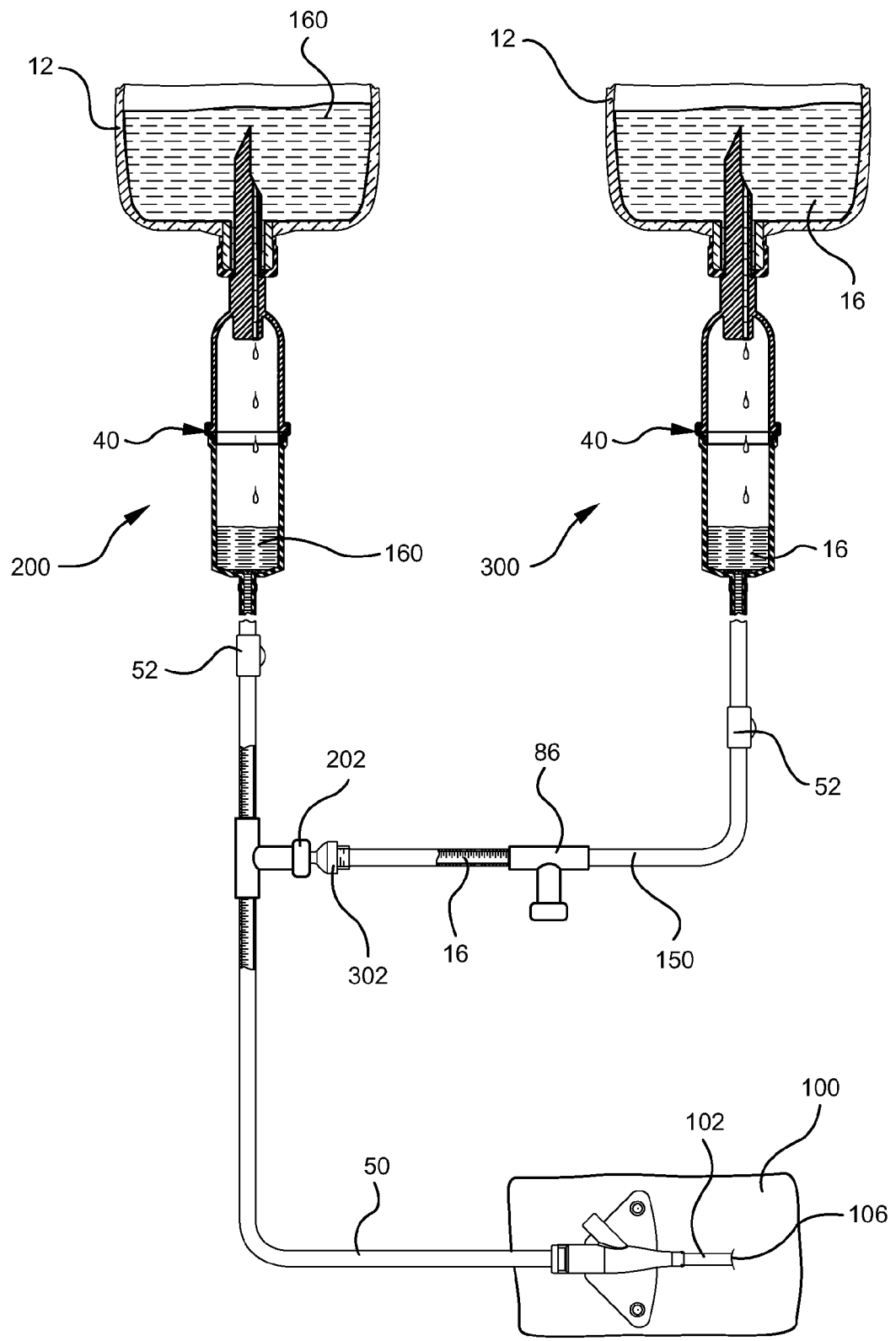
FIG. 14 is a cross-section view of an implementation of an IV set of the present invention used in conjunction with a primary IV delivery set.

Referring now to FIG. 14, a primary IV set 200 is combined with a secondary IV set 300 to provide a hazardous drug 16 to a patient 100 via a patient conduit 50. In this embodiment, the secondary IV set 300 is coupled to the primary IV set 200 via an inline access port 202. The inline access port 202 permits a hazardous drug 16 of the second IV set 300 to flow into the patient conduit 50 and into the patient 100. In some embodiments, the conduit line 150 of the second IV set 300 includes a closed luer tip 302 that automatically opens the fluid path upon attachment of the luer tip 302 to the inline access port 202. Additionally, upon removal of the luer tip 302 from the inline access port 202, the fluid pathway is closed and the luer tip 302 is cleaned by the flow of the priming fluid 160 through the patient conduit 50. In some embodiments, the inline access port 202 includes a set of threads for receiving a spinning lock nut of the luer tip 302. For these embodiments, the luer tip 302 is opened upon tightening of the lock nut around the set of threads, and is closed as the lock nut is loosened from the set of threads. In other embodiments, a proximal portion of the inline access port 202 is used to open and close the luer tip 302 at or near full engagement. Furthermore, in some embodiments the luer tip 302 includes a manual switch or valve to open and close fluid flow through the luer tip 302.

Following infusion of the hazardous drug 16, a roller clamp 52 of the second IV set 300 is actuated to occlude the conduit line 150 of the second IV set 300. The roller clamp 52 of the patient conduit 50 is then released to permit priming fluid 160 to flow through the patient conduit 50 and flush the remaining hazardous drug 16 into the patient 100. In some embodiments, a portion of luer tip 302 is positioned in the flow path of patient conduit 50 such that luer tip 302 is rinsed free of the hazardous drug 16 by priming fluid 160. In other embodiments, the inline access port 202 includes a deadspace which retains trace amounts of hazardous drug 16 following infusion. Therefore, in some embodiments a flush port 86 is incorporated into the conduit line 150 of the second IV set 300. The flush port 86 is accessed by a syringe to inject priming fluid 160 through a distal portion of the conduit line 150. Thus, the flush port 86 permits the deadspace of the inline access port 202 to be sufficiently flushed of the remaining hazardous drug 16. Following complete flushing of the hazardous drug from the inline access port 202 and the patient conduit 50, the catheter 102 may be safely removed from the patient 100 without exposure to the hazardous drug 16. Still further, in some embodiments inline access port 202 is a zero-deadspace connector. For example, in some embodiments a zero-deadspace connector eliminates deadspace between the flow path of patient conduit 50 and luer tip 302.

The present invention may be embodied in other specific forms without departing from its structures, methods, or other essential characteristics as broadly described herein and claimed hereinafter. Thus, the described embodiments are to be considered in all respects only as illustrative, and not restrictive. For example, some embodiments of the present invention may be used in conjunction with an IV pump. Other embodiments of the present invention may be configured to exclude the use of a drip chamber or a flow metering device, such as roller clamp or a dial-a-flow. The scope of the invention is, therefore, indicated by the appended claims, rather than by the foregoing description. All changes that come within the meaning and range of equivalency of the claims are to be embraced within their scope.

What is claimed is:

1. A device for storing and administering a hazardous solution to a patient via an intravenous needle, the device comprising:
    a spike comprising a first fluid pathway having an input and an output and a second fluid pathway having an input and an output, the spike being configured to insert within a primary fluid reservoir such that the input of the first fluid pathway and the output of the second fluid pathway are in fluid communication with a fluid within the primary fluid reservoir;
    an access port coupled to the spike, the access port forming the input to the second fluid pathway, wherein the access port is configured to receive a syringe for injecting a hazardous drug into the primary fluid reservoir and to irreversibly lock the syringe within the access port to prevent removal of the syringe from the access port thereby minimizing the risk of exposure to the hazardous drug;
    a drip chamber fluidly coupled to the spike and comprising an input and an output positioned at a bottom of the drip chamber, the drip chamber input being fluidly coupled to the output of the first fluid pathway, the output of the drip chamber being configured to receive a patient conduit; and
    a flushing port coupled to the drip chamber to thereby enable a flushing fluid to be injected directly into the drip chamber through the flushing port.

2. The device of claim 1, wherein the flushing port also comprises a priming port for injecting a priming solution into the drip chamber.

3. The device of claim 1, further comprising:
    a membrane covering the output of the drip chamber, wherein the membrane comprises a hydrophilic material that traps fluid to thereby prevent passage of air from the drip chamber to the output of the drip chamber.

4. The device of claim 3, wherein the membrane limits the flow rate of fluid from the drip chamber.

5. The device of claim 4, wherein the output of the drip chamber is connected to a patient conduit having a vent membrane attached thereto, and wherein the membrane is configured to provide a flow rate that matches a flow rate of the vent membrane.

6. The device of claim 1, wherein the flushing port extends from a sidewall of the drip chamber.

7. The device of claim 1, wherein the flushing port comprises a septum which seals the flushing port from an external environment.

8. The device of claim 1, wherein a hazardous drug is injected through the access port and into the primary fluid reservoir to mix with the fluid within the primary fluid reservoir and then pass into a patient via the drip chamber and the patient conduit, and wherein the fluid containing the hazardous drug is flushed from the drip chamber and patient conduit by injecting a flushing fluid through the flushing port.

9. A device for storing and administering a hazardous solution to a patient via an intravenous needle, the device comprising:
    a spike comprising a first fluid pathway having an input and an output and a second fluid pathway having an input and an output, the spike being configured to insert within a primary fluid reservoir such that the input of the first fluid pathway and the output of the second fluid pathway are in fluid communication with a fluid within the primary fluid reservoir;
    an access port forming the input of the second fluid pathway, the access port enabling a fluid containing a hazardous drug to be injected into the primary fluid reservoir;
    a drip chamber fluidly coupled to the spike and comprising an input and an output, the drip chamber input being fluidly coupled to the output of the first fluid pathway, and the output of the drip chamber being configured to receive a patient conduit;
    a priming port being positioned on a sidewall of the drip chamber, the priming port comprising a sealed second input to the drip chamber, wherein the priming port is configured to receive a syringe containing a second fluid such that the second fluid can be injected into the drip chamber via the priming port; and
    a vent, separate from the priming port, that is positioned on a sidewall of the drip chamber, the vent including a filter that is configured to filter hazardous gas that is generated as the hazardous drug passes through the drip chamber.

10. The device of claim 9, wherein the priming port is sealed via a septum.

11. The device of claim 10, wherein the syringe is inserted through the septum to inject the second fluid into the drip chamber.

12. The device of claim 9, wherein the second fluid comprises a non-hazardous drug.

13. The device of claim 9, wherein the second fluid comprises a flushing fluid for flushing a hazardous drug from the drip chamber.

14. The device of claim 9, wherein the access port is configured to receive a syringe for injecting a hazardous drug into the primary fluid reservoir and to lock the syringe within the access port to prevent removal of the syringe from the access port thereby minimizing the risk of exposure to the hazardous drug.

15. The device of claim 14, wherein a hazardous drug is injected through the access port and into the primary fluid reservoir to mix with the fluid within the primary fluid reservoir and then pass into a patient via the drip chamber and the patient conduit, and wherein the fluid containing the hazardous drug is flushed from the drip chamber and patient conduit by injecting a flushing fluid through the priming port.

16. The device of claim 9, wherein the second fluid is a priming fluid.

17. A method for administering a hazardous drug to a patient, the method comprising:
    priming an IV system in preparation for administering a hazardous drug to a patient, the IV system comprising:
        a spike comprising a first fluid pathway having an input and an output and a second fluid pathway having an input and an output, the spike being configured to insert within a primary fluid reservoir such that the input of the first fluid pathway and the output of the second fluid pathway are in fluid communication with a fluid within the primary fluid reservoir;
        an access port coupled to the spike, the access port forming the input to the second fluid pathway;
        a drip chamber fluidly coupled to the spike and comprising an input and an output positioned at a bottom of the drip chamber, the drip chamber input being fluidly coupled to the output of the first fluid pathway, the output of the drip chamber being configured to receive a patient conduit; and a priming/flushing port coupled to the drip chamber thereby providing direct fluid access to the drip chamber, the priming/flushing port including a septum that forms an airtight seal which maintains pressure within the drip chamber;

wherein the IV system is primed by inserting a device containing a priming fluid into the priming/flushing port to bypass the septum and injecting the priming fluid into the drip chamber;

inserting the spike of the IV system into a primary fluid reservoir containing an intravenous fluid;

inserting a device containing a hazardous drug into the access port and injecting the hazardous drug into the primary fluid reservoir to be mixed with the intravenous fluid for delivery through the IV system into the vasculature of a patient; and after the intravenous fluid containing the hazardous drug has passed through the IV system, inserting a device containing a flushing fluid into the priming/flushing port to bypass the septum and injecting the flushing fluid into the drip chamber such that the flushing fluid washes residual intravenous fluid containing the hazardous drug through the IV system and into the vasculature of the patient.

18. The method of claim 17, wherein the access port locks the device containing the hazardous drug within the access port to minimize the risk of exposure to any hazardous drug that remains on the device after the hazardous drug is injected into the primary fluid reservoir.

* * * * *